(12) United States Patent
Yamada et al.

(10) Patent No.: US 10,978,644 B2
(45) Date of Patent: Apr. 13, 2021

(54) ORGANIC COMPOUND AND ORGANIC PHOTOELECTRIC CONVERSION ELEMENT INCLUDING THE SAME

(71) Applicant: CANON KABUSHIKI KAISHA, Tokyo (JP)

(72) Inventors: Naoki Yamada, Inagi (JP); Jun Kamatani, Tokyo (JP); Hiroki Ohrui, Kawasaki (JP); Hironobu Iwawaki, Yokohama (JP); Masumi Itabashi, Yamato (JP); Yosuke Nishide, Kawasaki (JP); Hirokazu Miyashita, Ebina (JP); Satoru Shiobara, Hiratsuka (JP); Tomona Yamaguchi, Tokyo (JP); Tetsuo Takahashi, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 120 days.

(21) Appl. No.: 16/243,500

(22) Filed: Jan. 9, 2019

(65) Prior Publication Data

US 2019/0148644 A1    May 16, 2019

Related U.S. Application Data

(63) Continuation of application No. PCT/JP2017/024986, filed on Jul. 7, 2017.

(30) Foreign Application Priority Data

Jul. 21, 2016 (JP) .............................. JP2016-143317

(51) Int. Cl.
*H01L 51/00* (2006.01)
*C07D 409/06* (2006.01)
(Continued)

(52) U.S. Cl.
CPC ........ *H01L 51/0061* (2013.01); *C07D 333/20* (2013.01); *C07D 333/22* (2013.01);
(Continued)

(58) Field of Classification Search
CPC .. C07D 333/20; C07D 333/22; C07D 409/06; C07D 409/14; H01L 27/307;
(Continued)

(56) References Cited

U.S. PATENT DOCUMENTS 7,731,796 B2    6/2010    Jung et al.
8,525,577 B2    9/2013    Yofu et al.
(Continued)

FOREIGN PATENT DOCUMENTS

CN    101787020 A    7/2010
CN    101962380 A    2/2011
(Continued)

OTHER PUBLICATIONS

Machine translation of JP 2012-051854 A (Year: 2012).*
(Continued)

*Primary Examiner* — Ramsey Zacharia
(74) *Attorney, Agent, or Firm* — Venable LLP

(57) ABSTRACT

The present disclosure provides an organic compound expressed by the following General Formula 1:

(Continued)

In General Formula 1, a partial structure Z1 represents a condensed polycyclic group that may include a nitrogen atom in a skeleton, and that includes at least one of a five-membered ring and a six-membered ring. The partial structure Z1 may include, as a substituent, a carbonyl group, a dicyanovinylidene group, a halogen atom, a cyano group, an alkyl group, an alkoxy group, an aromatic heterocyclic group, or an aryl group. $R_1$ and $R_2$ represent an alkyl group, aryl group, an aromatic heterocyclic group, a halogen group, or a cyano group. $Ar_1$ represents an arylene group or a divalent aromatic heterocyclic group, and $Ar_2$ and $Ar_3$ represent an aryl group or an aromatic heterocyclic group. n represents an integer of 1 to 4.

19 Claims, 4 Drawing Sheets

(51) Int. Cl.

| | |
|---|---|
| *C07D 409/14* | (2006.01) |
| *C07D 333/22* | (2006.01) |
| *H01L 51/46* | (2006.01) |
| *C07D 333/20* | (2006.01) |
| *H01L 51/42* | (2006.01) |
| *H01L 27/30* | (2006.01) |
| *H04N 5/378* | (2011.01) |

(52) U.S. Cl.
CPC ......... *C07D 409/06* (2013.01); *C07D 409/14* (2013.01); *H01L 51/0047* (2013.01); *H01L 51/0053* (2013.01); *H01L 51/0068* (2013.01); *H01L 51/4273* (2013.01); *H01L 27/307* (2013.01); *H01L 51/006* (2013.01); *H01L 51/0046* (2013.01); *H01L 51/0059* (2013.01); *H01L 51/0072* (2013.01); *H01L 51/4253* (2013.01); *H04N 5/378* (2013.01); *Y02E 10/549* (2013.01)

(58) Field of Classification Search
CPC ............. H01L 51/0046; H01L 51/0047; H01L 51/0053; H01L 51/0059; H01L 51/006; H01L 51/0061; H01L 51/0068; H01L 51/0072; H01L 51/4253; H01L 51/4273; H04N 5/378; Y02E 10/549
See application file for complete search history.

(56) References Cited

U.S. PATENT DOCUMENTS 9,070,887 B2  6/2015  Yofu et al.
2006/0119724 A1* 6/2006 Inuiya .................. H04N 9/045
                                                   348/311
2018/0159059 A1* 6/2018 Takemura ......... H01L 27/14645
2019/0013469 A1  1/2019 Miyashita et al.

FOREIGN PATENT DOCUMENTS

| JP | 2003-238559 A | 8/2003 |
|---|---|---|
| JP | 2005-008558 A | 1/2005 |
| JP | 2006-063043 A | 3/2006 |
| JP | 2007-091714 A | 4/2007 |
| JP | 2007-201408 A | 8/2007 |
| JP | 2009-079092 A | 4/2009 |
| JP | 2011-500882 A | 1/2011 |
| JP | 2011-77198 A | 4/2011 |
| JP | 2012-051854 A | 3/2012 |
| WO | 2009/051390 A1 | 7/2009 |
| WO | 2013/168084 A1 | 11/2013 |
| WO | 2016/066494 A1 | 5/2016 |
| WO | 2018/016354 A1 | 1/2018 |

OTHER PUBLICATIONS

Antoine Lelie'ge et al., "Structural modulation of internal charge transfer in Small Molecular Donors for Organic Solar Cells," 48(71) Chem. Comm. 8907-8909 (2012).
Chunxuan Qi, et al., "Study of Red-Emission Piezochromic Materials Based on Triphenylamine," 81(7) Chem Plus Chem 637-645 (Jun. 2016).
Masaya Hirade et al., Effects of Intramolecular Donor-Acceptor Interactions on Bimolecular Recombination Small-Molecule Organic Photovoltaic Cells, 117(10) J. Phys. Chem. C 4986-4991 (2013).
Akhil Gupta et al., "Molecular engineering for panchromatic absorbing oligothiophene donor-π-acceptor organic semiconductors," 68(46) Tetrahedron 9440-9447 (Sep. 2012).
Philippe Leriche et al., "Molecular Engineering of the Internal Charge Transfer in Thiophene-Triphenylamine Hybrid π-Conjugated Systems," 72(22) J. Org. Chem. 8332-8336 (2007).
Sophie Roquet et al., "Triphenylamine-Thienylenevinylene Hybrid Systems with Internal Charge Transfer as Donor Materials for Heterojunction Solar Cells," 128(10) J. Am. Chem. Soc. 3459-3466 (Feb. 2006).
International Search Report in International Application No. PCT/JP2017/024986 (dated Aug. 2017).
International Preliminary Report on Patentability in International Application No. PCT/JP2017/024986 (dated Jan. 31, 2019).
Yamada et al., U.S. Appl. No. 16/051,724, filed Aug. 1, 2018.
Nishide et al., U.S. Appl. No. 16/163,757, filed Oct. 18, 2018.
Nishide et al., U.S. Appl. No. 16/106,534, filed Aug. 21, 2018.
Yamada et al., U.S. Appl. No. 16/130,029, filed Sep. 13, 2018.
Notification of Reasons for Refusal in Japanese Application No. 2016-143317 (dated Jun. 23, 2020).

* cited by examiner

ORGANIC COMPOUND AND ORGANIC PHOTOELECTRIC CONVERSION ELEMENT INCLUDING THE SAME

CROSS-REFERENCE TO RELATED APPLICATIONS

This application is a Continuation of International Patent Application No. PCT/JP2017/024986, filed Jul. 7, 2017, which claims the benefit of Japanese Patent Application No. 2016-143317, filed Jul. 21, 2016, both of which are hereby incorporated by reference herein in their entirety.

BACKGROUND OF THE INVENTION

Field of the Invention

The present invention relates to an organic compound, and an organic photoelectric conversion element, an organic photoelectric conversion apparatus, an optical area sensor, an image pickup element, and an image pickup apparatus including the organic compound.

Description of the Related Art

For an image pickup element, a planar light reception element has been widely used. In the planar light reception element, photoelectric conversion units are arranged two-dimensionally as pixels in a semiconductor and signals resulted from photoelectric conversion of these pixels are subjected to charge transfer or readout through a CCD circuit or a CMOS circuit. On the other hand, a photodiode including an organic compound in a photoelectric conversion unit has been known. Chemical Communications 2012, vol. 48 (71), p. 8907-8909 describes an element including a compound R-1 in an organic photoelectric conversion layer. Japanese Patent Application Laid-Open No. 2011-77198 describes an element including a compound R-2 in an organic photoelectric conversion layer.

R-1

R-2

However, the organic compounds according to Japanese Patent Application Laid-Open No. 2011-77198 and Chemical Communications 2012, vol. 48 (71), p. 8907-8909 are insufficient in sensitivity in light absorption, especially the sensitivity to light on a long wavelength side.

In view of the above, an object of the present invention is to provide an organic compound with high sensitivity in the light absorption.

SUMMARY OF THE INVENTION

An organic compound according to the present invention is expressed by the following General Formula 1.

[1]

In General Formula 1, a partial structure Z1 represents a condensed polycyclic group that may include a nitrogen atom in a skeleton, and that includes at least one of a five-membered ring and a six-membered ring. The partial structure Z1 may include, as a substituent, a carbonyl group, a dicyanovinylidene group, a halogen atom, a cyano group, an alkyl group, an alkoxy group, an aromatic heterocyclic group, or an aryl group.

$R_1$ and $R_2$ represent an alkyl group, aryl group, an aromatic heterocyclic group, a halogen group, or a cyano group, $Ar_1$ represents an arylene group or a divalent aromatic heterocyclic group, and $Ar_2$ and $Ar_3$ represent an aryl group or an aromatic heterocyclic group. $Ar_1$ to $Ar_3$ may include, as a substituent, a halogen atom, a cyano group, an alkyl group, an alkoxy group, an aromatic heterocyclic group, or an aryl group.

n represents an integer of 1 to 4.

Further features of the present invention will become apparent from the following description of exemplary embodiments with reference to the attached drawings.

DESCRIPTION OF THE EMBODIMENTS

<Organic Compound>

Figure 1A:
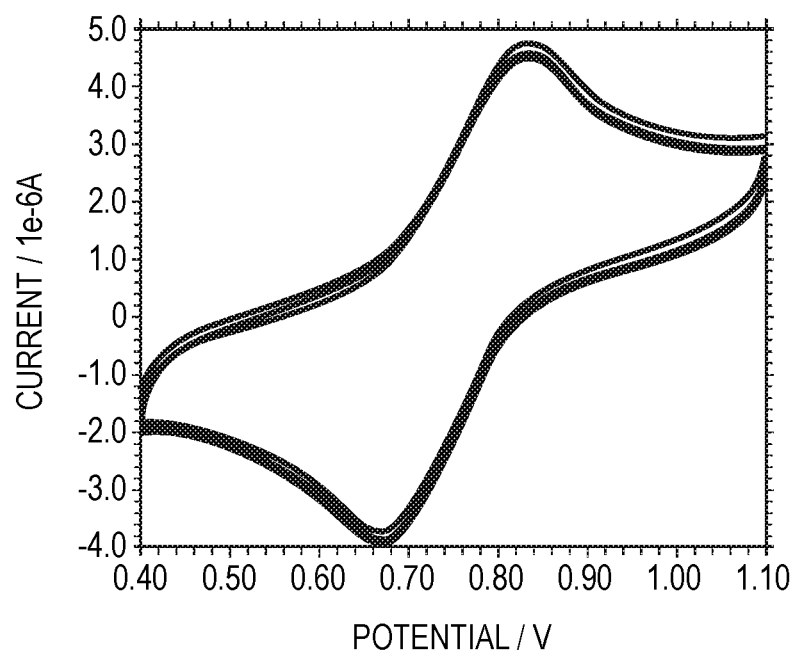
FIG. 1A shows results of cyclic voltammetry of an example compound A-1.

An organic compound according to the present invention is expressed by the following General Formula 1:

[1]

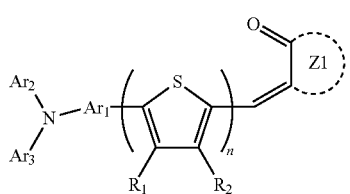

In General Formula 1, a partial structure Z1 refers to a structure shown below. In the partial structure Z1, * represents a carbon atom to which a carbon atom-carbon double bond is bonded.

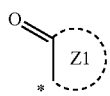

The partial structure Z1 represents a condensed polycyclic group that may include a nitrogen atom in a skeleton and that includes at least one of a five-membered ring and a six-membered ring. The partial structure Z1 may include, as a substituent, a carbonyl group, a dicyanovinylidene group, a halogen atom, a cyano group, an alkyl group, an alkoxy group, an aromatic heterocyclic group, or an aryl group.

The partial structure Z1 may be a structure expressed by, for example, any of the following General Formulae 11 to 19:

[11]

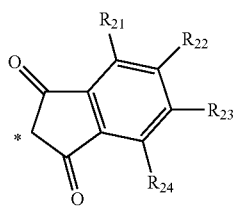

[12]

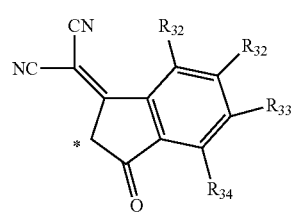

[13]

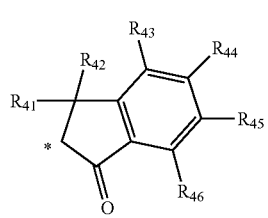

[14]

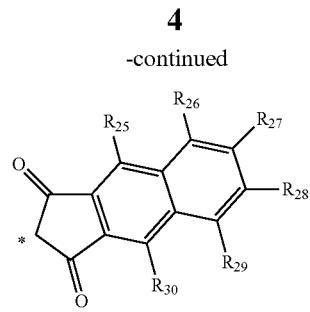

[15]

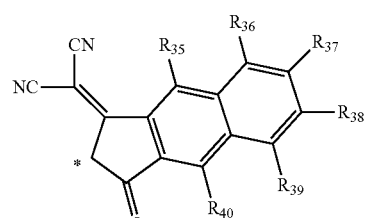

[16]

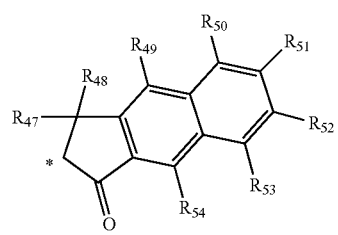

[17]

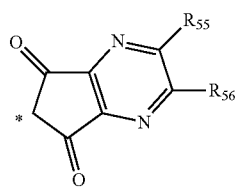

[18]

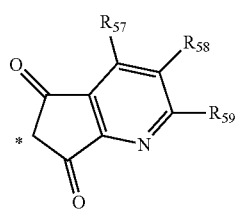

[19]

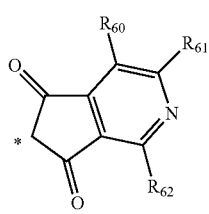

In General Formulae 11 to 19, $R_{21}$ to $R_{62}$ are selected from a hydrogen atom, a halogen atom, a cyano group, an alkyl group, an alkoxy group, an aromatic heterocyclic group, and an aryl group.

Examples of the halogen atom as $R_{21}$ to $R_{62}$ in General Formulae 11 to 19 include a fluorine atom, a chlorine atom, a bromine atom, and an iodine atom, and a fluorine atom is preferable.

Examples of the alkyl group as $R_{21}$ to $R_{62}$ in General Formulae 11 to 19 include a methyl group, an ethyl group, an n-propyl group, an iso-propyl group, an n-butyl group, an s-butyl group, a t-butyl group, an octyl group, a 1-adamantyl group, and a 2-adamantyl group, and an alkyl group with one or more and four or less carbons, such as a methyl group, an ethyl group, an n-propyl group, an iso-propyl group, an n-butyl group, an s-butyl group, or a t-butyl group, is preferable.

Examples of the alkoxy group as $R_{21}$ to $R_{62}$ in General Formulae 11 to 19 include a methoxy group, an ethoxy group, an n-propoxy group, an iso-propoxy group, an n-butoxy group, an s-butoxy group, a t-butoxy group, an octyloxy group, a 1-adamantyloxy group, and a 2-adamantyloxy group, and an alkoxy group with one or more and four or less carbons, such as a methoxy group, an ethoxy group, an n-propoxy group, an iso-propoxy group, an n-butoxy group, an s-butoxy group, or a t-butoxy group, is preferable.

Examples of the aromatic heterocyclic group as $R_{21}$ to $R_{62}$ in General Formulae 11 to 19 include a pyridyl group, a pyradinyl group, a pyrimidyl group, a triazinyl group, a pyrrolyl group, a furanyl group, a thienyl group, an imidazole group, a pyrazole group, an oxazole group, a thiazole group, an imidazolinyl group, a thiazine group, a quinolyl group, an isoquinolyl group, an azaphenanthrenyl group, a phenanthrolinyl group, a benzothienyl group, a dibenzothienyl group, a benzofuranyl group, and a dibenzofuranyl group, and a pyridyl group, a pyradinyl group, or a pyrimidyl group is preferable.

Examples of the aryl group as $R_{21}$ to $R_{62}$ in General Formulae 11 to 19 include a phenyl group, a biphenyl group, a terphenyl group, a naphthyl group, a phenanthrenyl group, a chrysenyl group, a pyrenyl group, a fluorenyl group, and a fluoranthenyl group, and particularly, a phenyl group, a biphenyl group, or a naphthyl group is preferable.

The alkyl group, the alkoxy group, the aromatic heterocylic group, and the aryl group may further include a substitute, and in this case, the substitute is selected from a halogen atom, a cyano group, an alkyl group, and an aryl group. The halogen atom as the substituent is preferably a fluorine atom, and the alkyl group as the substituent is preferably an alkyl group with one or more and four or less carbons, and a methyl group, an ethyl group, an iso-propyl group, an s-butyl group, or a t-butyl group is preferable. The aryl group is preferably a phenyl group, a naphthyl group, a phenanthrenyl group, a chrysenyl group, a pyrenyl group, a fluorenyl group, and a fluoranthenyl group, and a phenyl group is particularly preferable.

In the organic compound expressed by General Formula 1, $R_1$ and $R_2$ represent a hydrogen atom, an alkyl group, an aryl group, an aromatic heterocyclic group, a halogen atom, or a cyano group. The alkyl group, the aryl group, the aromatic heterocyclic group, and the halogen atom may be similar to those represented as $R_{21}$ to $R_{62}$ in the partial structure Z1.

In the organic compound expressed by General Formula 1, $Ar_1$ represents an arylene group or a divalent aromatic heterocyclic group and $Ar_2$ and $Ar_3$ represent an aryl group or an aromatic heterocyclic group. The arylene group and the divalent aromatic heterocyclic group may be a divalent group corresponding to the aryl group or the aromatic heterocyclic group described in regard to the partial structure Z1. The aryl group or the aromatic heterocyclic group may be similar to those described in regard to the partial structure Z1. Among these groups, $Ar_1$ preferably represents a phenylene group, a biphenylene group, or a naphthylene group, and $Ar_2$ and $Ar_3$ preferably represent independently any one of a phenyl group, a biphenyl group, and a naphthyl group. $Ar_1$ to $Ar_3$ may have a halogen atom, a cyano group, an alkyl group, an alkoxy group, an aromatic heterocyclic group, or an aryl group as a substituent. The halogen atom, the alkyl group, the alkoxy group, the aromatic heterocyclic group, and the aryl group as the substituent may be similar to those described in regard to the partial structure Z1.

In General Formula 1, n represents an integer of 1 to 4 expressing the number of repeating a thiophene part that is replaced by $R_1$ and $R_2$, and is preferably an integer of 1 to 3, more preferably 1 or 2, and much more preferably 1.

Examples of the organic compound according to the present invention are shown below:

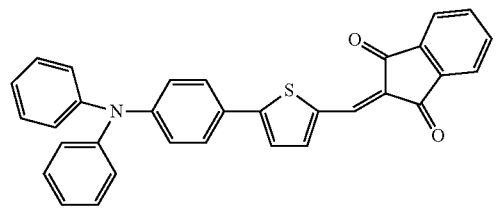

A-1

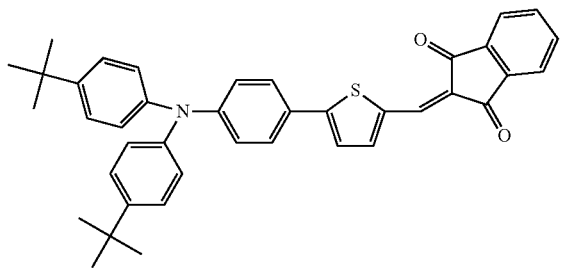

A-2

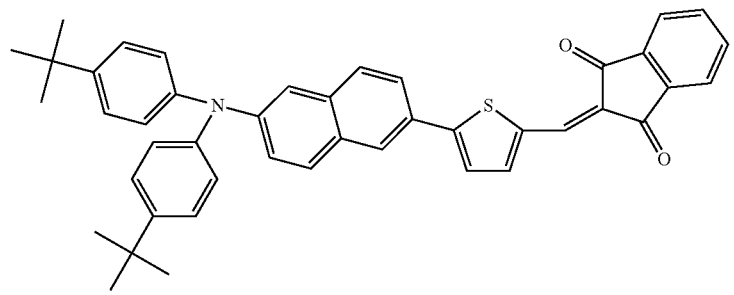

A-3

-continued
A-4
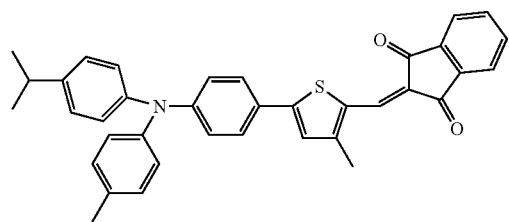
A-5
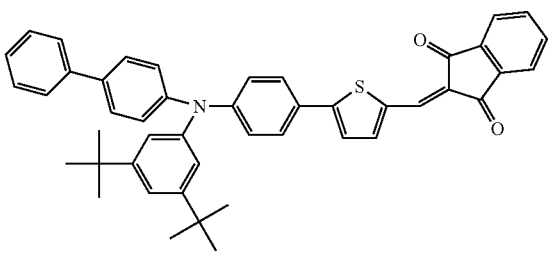
A-6
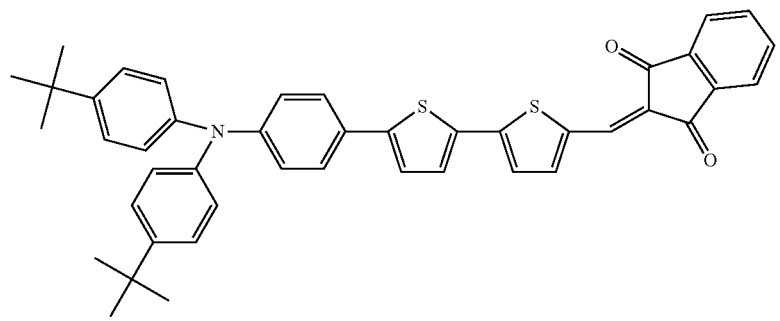
A-7
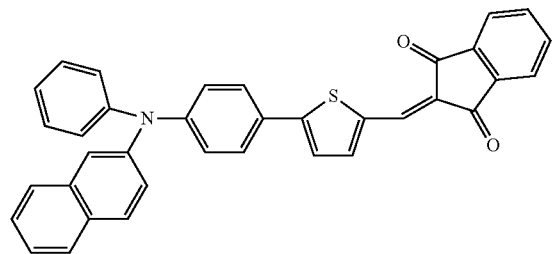
A-8
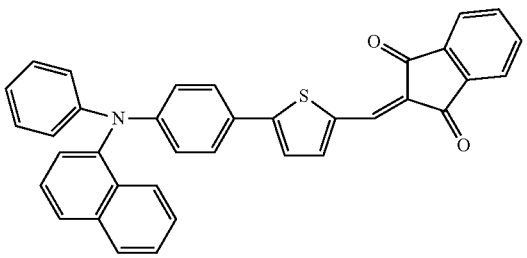
A-9
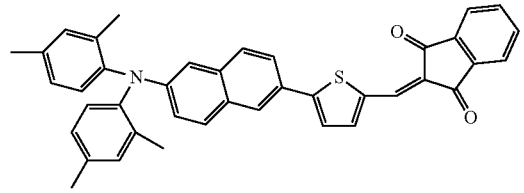
A-10
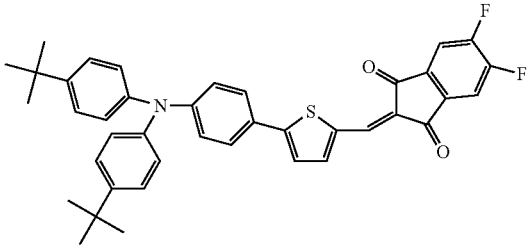
A-11
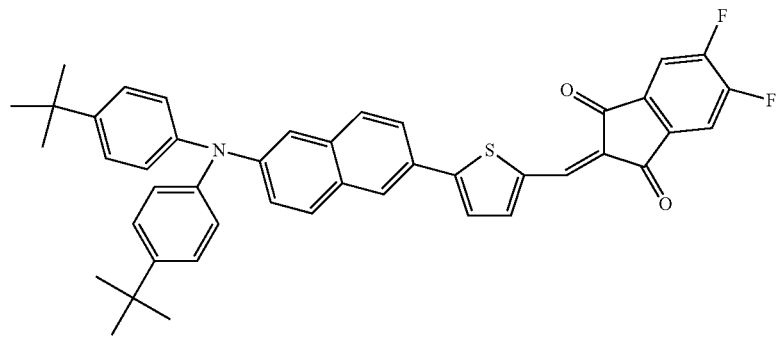

-continued
A-12
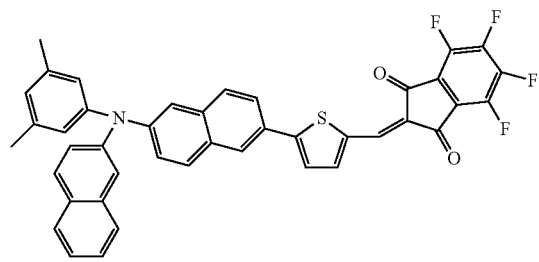
A-13
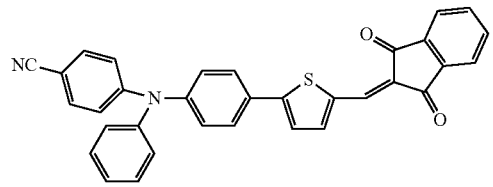
A-14
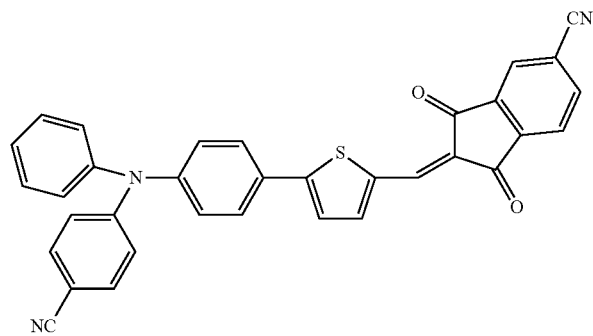
A-15
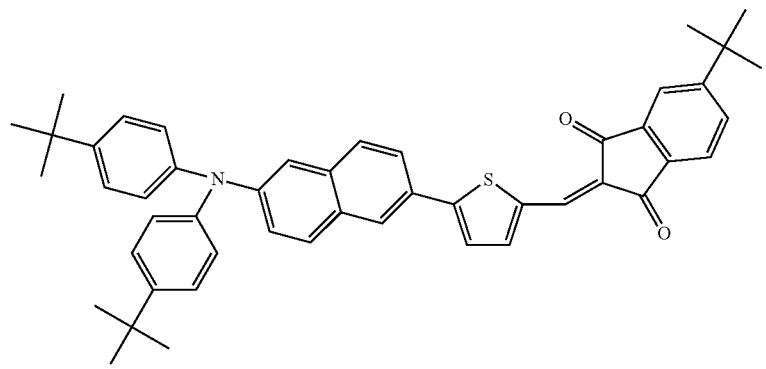
A-16
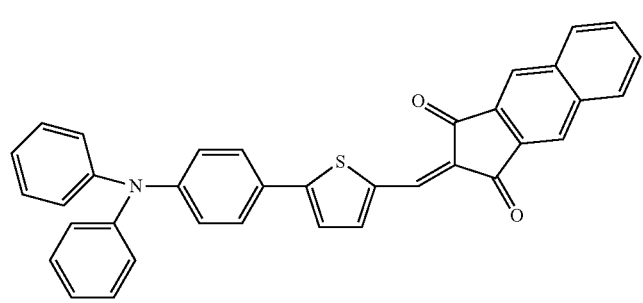
A-17
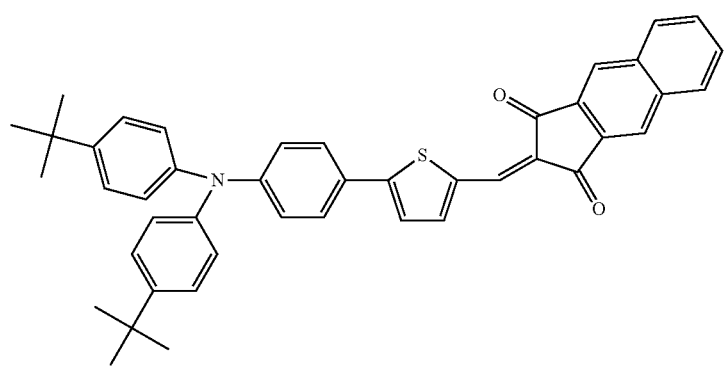

-continued
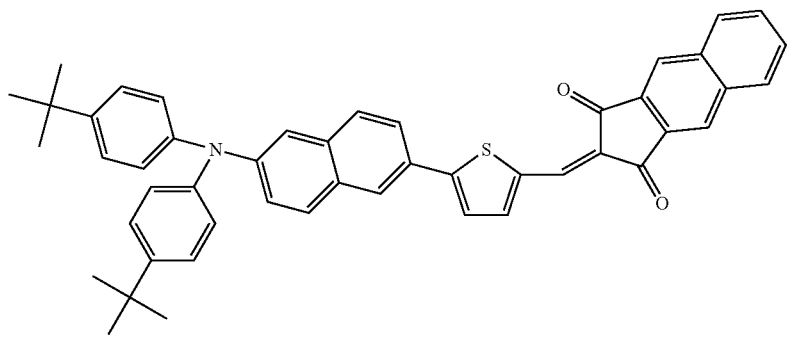
A-18
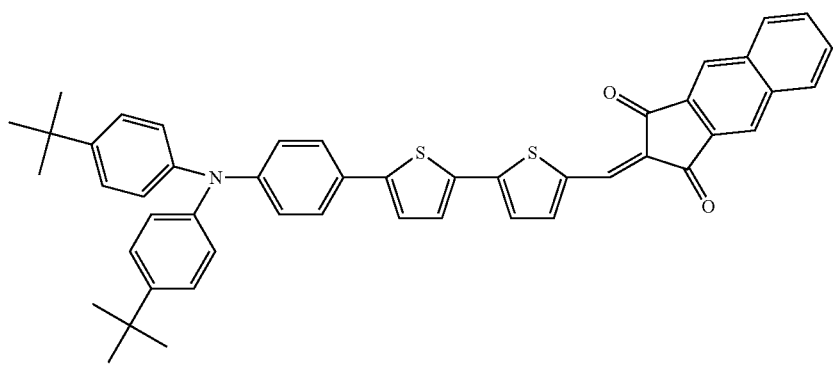
A-19
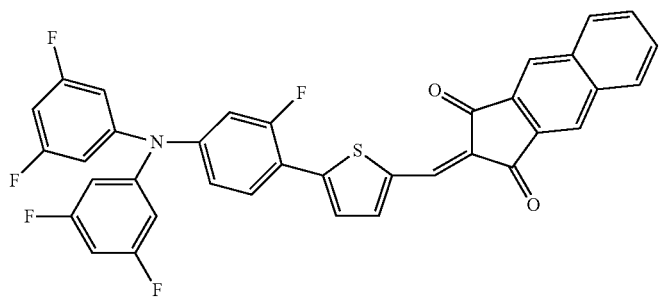
A-20
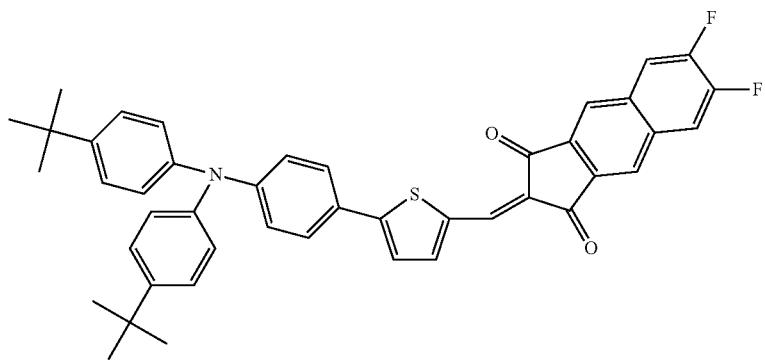
A-21
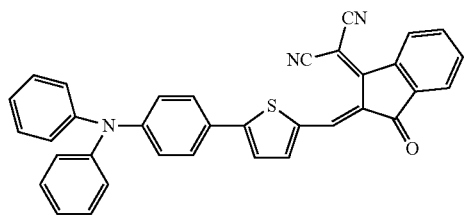
B-1
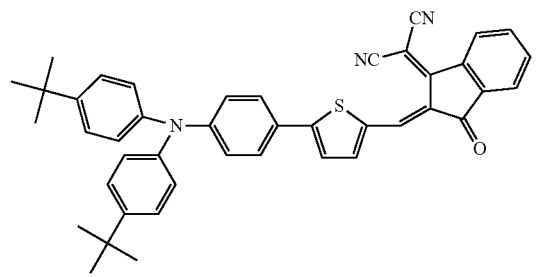
B-2

B-3
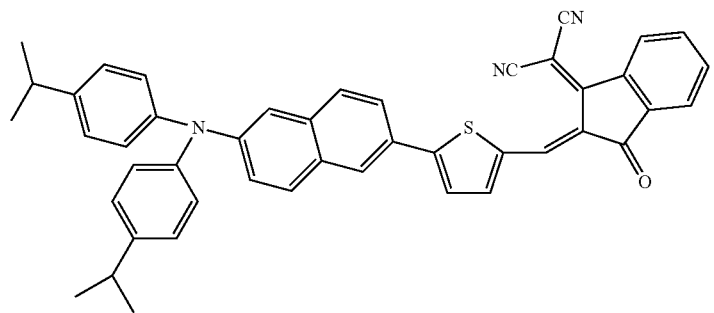
B-4 B-5
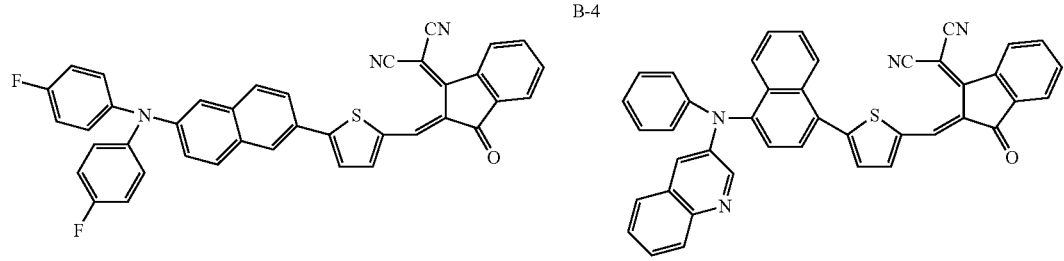
B-6
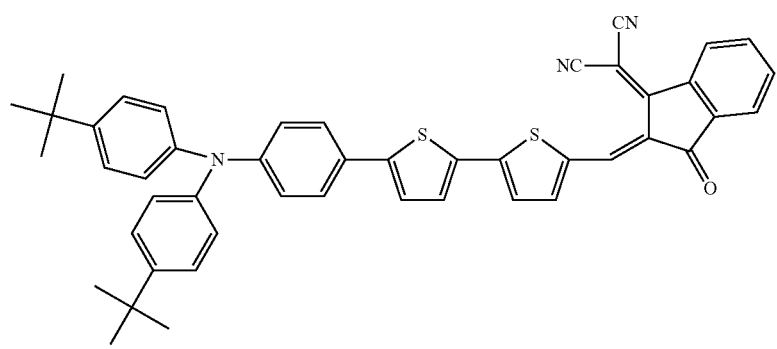
B-7
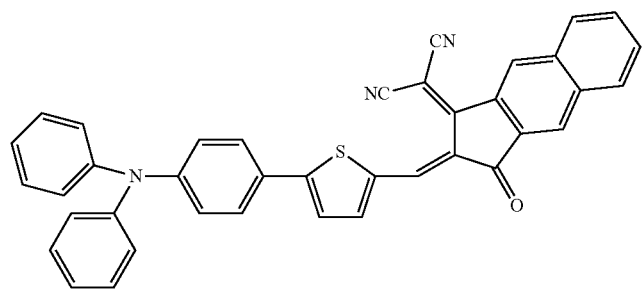
B-8 B-9
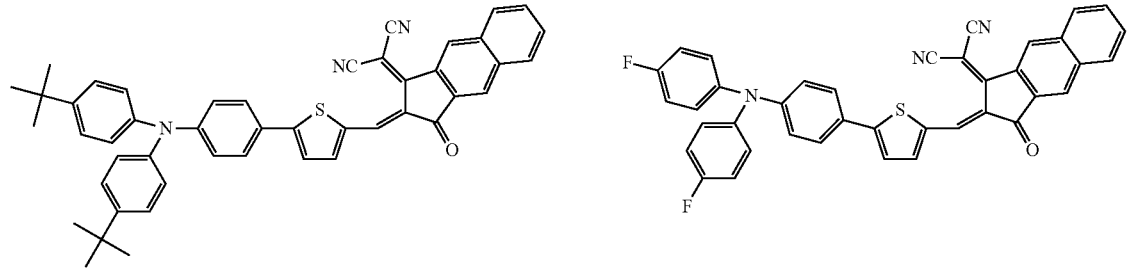

-continued
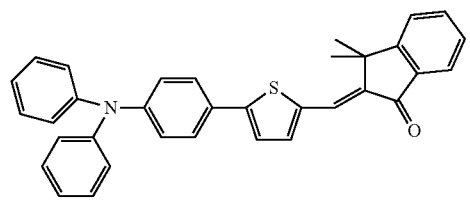
C-1
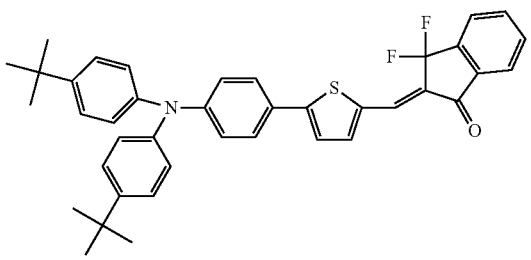
C-2
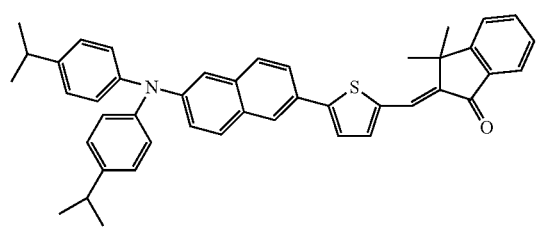
C-3
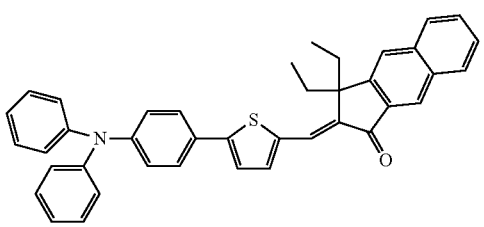
C-4
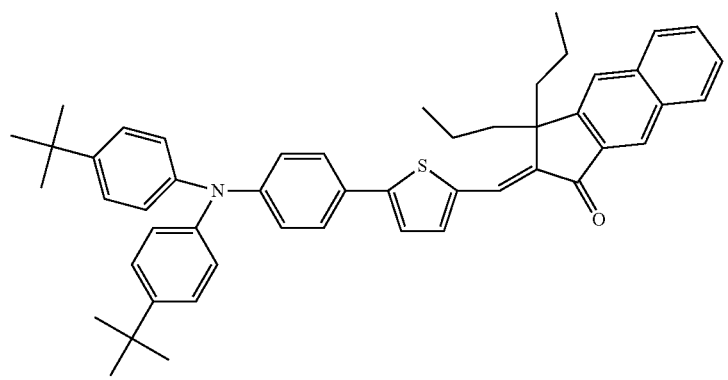
C-5
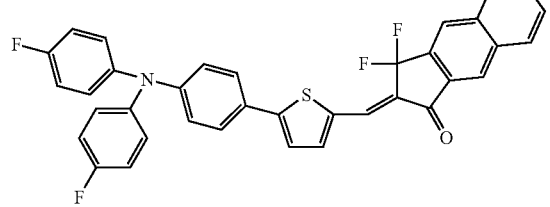
C-6
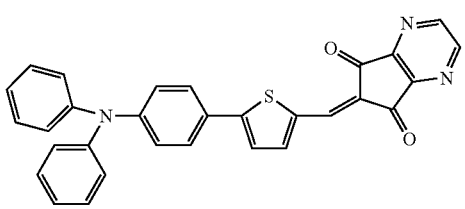
D-1
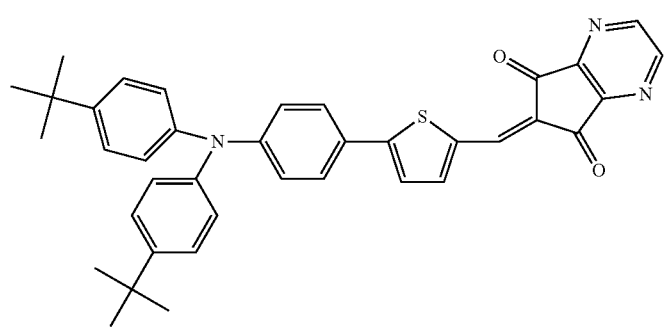
D-2

-continued
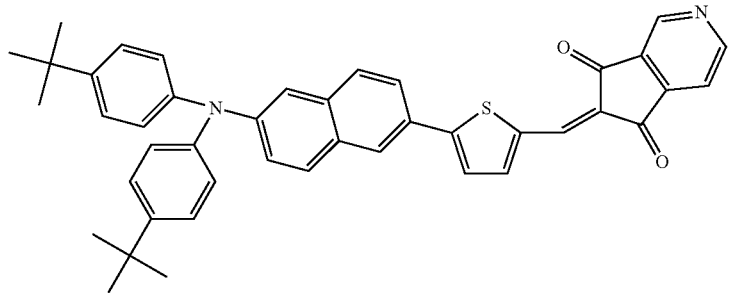
D-3
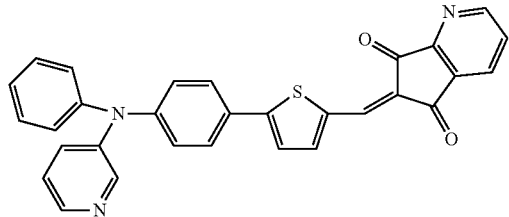
D-4
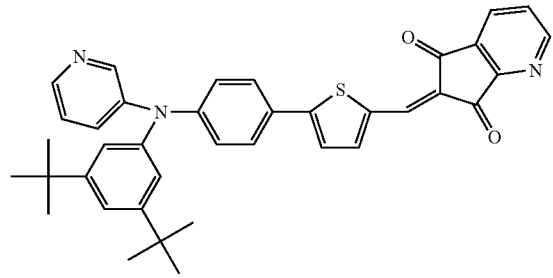
D-5
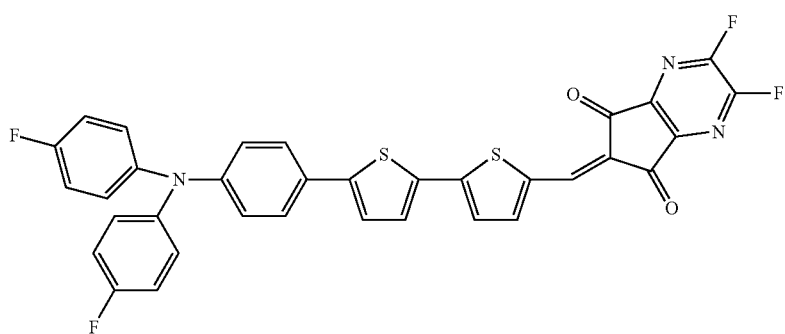
D-6
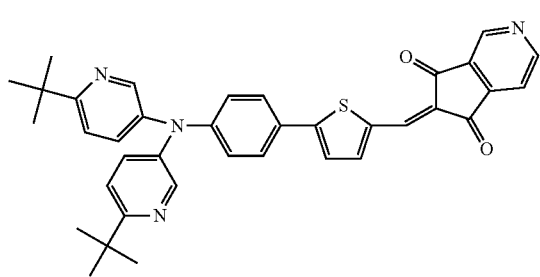
D-7
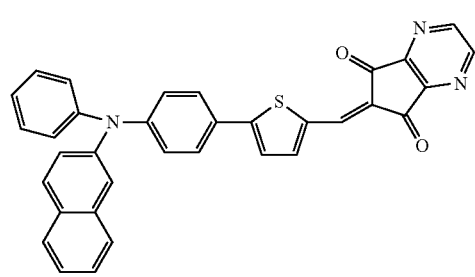
D-8
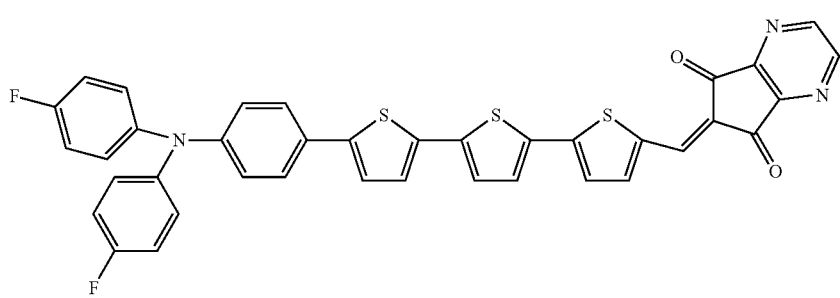
D-9

The organic compound according to the present invention can be synthesized in accordance with the following scheme, for example:

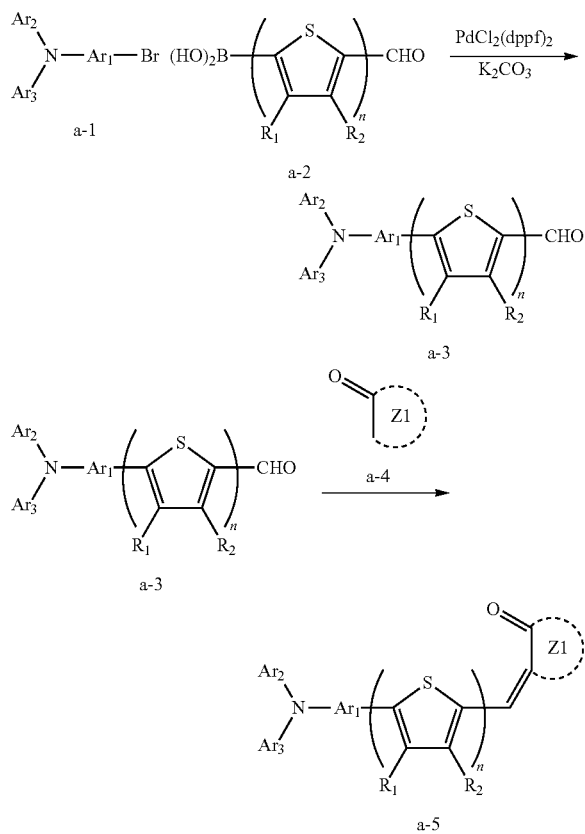

Through Suzuki coupling of a compound a-1 and a compound a-2, an intermediate a-3 is synthesized. A Pd-based catalyst is preferably used and particularly, $PdCl_2(dppf)_2$ is preferable as a catalyst. The compound a-1 may include a substituent that reacts with boronic acid instead of a bromine body, and may include another halogen body, for example. An organic compound a-5 according to the present invention can be synthesized by reaction of the intermediate a-3 and a ketone body a-4 corresponding to the partial structure Z1 in a base. The organic compound according to the present invention may be synthesized by any other synthesis method. In accordance with the above method, various kinds of organic compounds a-5 according to the present invention can be synthesized.

An example compound A-1 corresponding to one example of the organic compound according to the present invention is compared with the compound R-1 according to Chemical Communications 2012, vol. 48 (71), p. 8907-8909 the compound R-2 according to Japanese Patent Application Laid-Open No. 2011-77198.

(1) Absorption of a Long Wavelength Side of a Visible Light Region (Absorption Wavelength and Molar Absorption Coefficient)

In a case where light in a visible light region is captured as a charge signal in an organic photoelectric conversion film, it is preferable that light can be absorbed in the entire visible light region from 380 to 750 nm. In particular, the absorption sensitivity in a red region (600 to 750 nm) is preferably high. Specifically, it is preferable that the absorption end on the long wavelength side in a thin film state (position where the absorption spectrum starts to rise) is in the red region (600 nm or more) and the absorption end on the long wavelength side in a chloroform dilute solution (solution with a concentration of less than $5 \times 10^{-5}$ mol/L) is at 580 nm or more, more preferably 600 nm or more. In this case, the maximum absorption wavelength of the chloroform dilute solution is preferably 515 to 615 nm. At the maximum absorption wavelength, the molar absorption coefficient is preferably high.

Table 1 shows the maximum absorption wavelengths of the example compound A-1 and the comparative compounds R-1 and R-2 in the chloroform dilute solution.

TABLE 1

|  | Example compound A-1 | Comparative compound R-1 | Comparative compound R-2 |
|---|---|---|---|
| Maximum absorption wavelength in chloroform dilute solution [nm] | 532 | 507 | 518 |
| Molar absorption coefficient [M−1 cm−1] | 42550 | 37600 | 26660 |

The comparative compound R-1 has a maximum absorption wavelength of 507 nm, and has a low capability of absorbing the light on the long wavelength side in the visible light region, and in particular, it is difficult to sense the light in the long wavelength region. On the other hand, the example compound A1 has a maximum absorption wavelength of 532 nm and has a capability of absorbing the light on the long wavelength side in the visible light region, and the molar absorption coefficient at 532 nm is high. This is because of the high electron-withdrawing property of the electron-withdrawing group, and as the substituent has the higher electron-withdrawing property, the LUMO level is stabilized more and the absorption spectrum becomes longer in wavelength. That is to say, it is considered that a dicyano group of the comparative compound R-1 is lower in electron-withdrawing property than a condensed polycyclic structure (partial structure Z1) including ketone of the organic compound according to the present invention. Similarly, the comparative compound R-2 in which thiophene is directly bonded to the amino group has a maximum absorption wavelength that is shorter than that of the example compound A-1, and has a very low molar absorption coefficient.

Since the end of the absorption spectrum of the organic compound according to the present invention exists on the long wavelength side, the light in a wider range can be absorbed. The organic compound according to the present invention has a molar absorption coefficient of 40000 or more, and has high sensitivity in light absorption.

In a case of employing the organic compound according to the present invention for an organic photoelectric conversion element, using an organic n-type semiconductor such as a fullerene derivative as an electron acceptor can further increase the absorption sensitivity particularly on the short wavelength side from 380 nm to 500 nm in addition to the absorption region of the organic compound according to the present invention. Thus, a panchromic performance becomes preferable. The panchromic performance refers to the capability of having high absorption sensitivity in the entire visible light region.

In addition, the organic compound according to the present invention is a compound that has a high electron donating property by including an amino group. In addition, by additionally using the organic n-type semiconductor such as a fullerene derivative for the photoelectric conversion layer, the organic compound according to the present invention can provide the function as an electron donor and the preferable photoelectric conversion. That is to say, with the panchromic performance and the high photoelectric conversion characteristic, the organic compound according to the present invention has the excellent photoelectric conversion characteristic in the entire wavelength region. Alternatively, the organic compound according to the present invention can be used in combination with a plurality of electron donor materials.

The organic compound according to the present invention may be used as an electron acceptor of the photoelectric conversion layer together with the electron donor material. In this case, one kind of, or a plurality of kinds of organic compounds according to the present invention can be used as the electron acceptor. In the organic photoelectric conversion element, the electron donor and the electron acceptor absorb light and the charge separation occurs; then, holes and electrons are transported by the electron donors and the electron acceptors, respectively to the electrodes. In a case where the plurality of kinds of organic compounds according to the present invention is mixed in the photoelectric conversion layer, a trap or a defect may be generated in a charge transport level. Therefore, in the case where the plurality of kinds of organic compounds according to the present invention is used as the electron acceptor of the photoelectric conversion layer, it is preferable to use the combination including the organic compounds according to the present invention where the trap or defect is not generated easily.

(2) Durability Against Repeated Use (Oxidation-Reduction Stability)

When the organic photoelectric conversion element absorbs light and the charge separation occurs, radical cationic species and radical anionic species are generated and these species need to be collected in both electrodes. Therefore, in particular, in the case of using the organic compound according to the present invention together with the organic n-type semiconductor such as a fullerene derivative, using the organic compound according to the present invention as the light-absorbing compound with higher oxidation-reduction stability can improve the durability of the organic photoelectric conversion element against the repeated use.

Figure 1B:
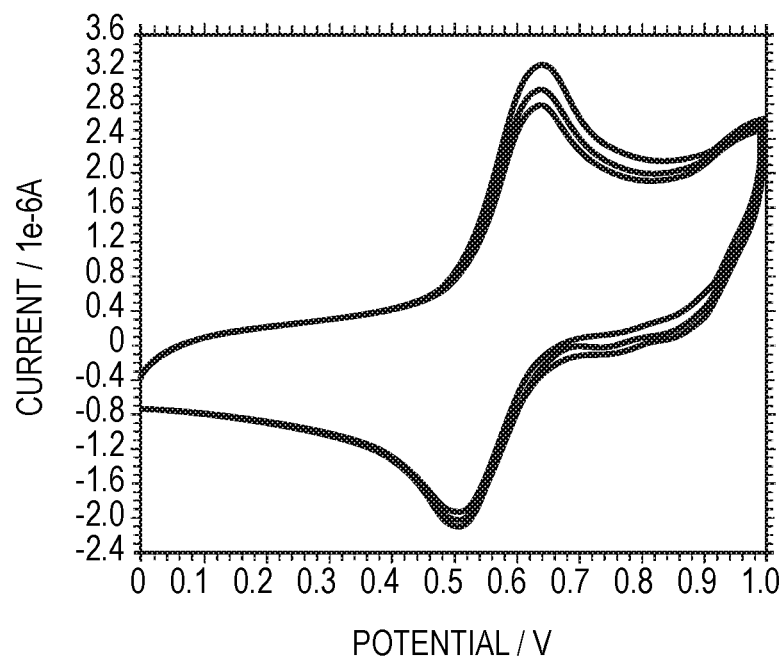
FIG. 1B shows results of cyclic voltammetry of a comparative compound R-2.

The example compound A-1 corresponding to one of the organic compounds according to the present invention was subjected to four-successive sweeping evaluations of one electron oxidation using cyclic voltammetry (CV). CV measurement results of the example compound A-1 are shown in FIG. 1A. As shown in FIG. 1A, a reversible oxidation wave was obtained as the results of the CV measurement of the example compound A-1, and the waveform hardly changed. After repeated sweeping, the example compound A-1 hardly deteriorated. This indicates that the example compound A-1 can exist stability without causing reaction or decomposition by one electron oxidation. On the other hand, the comparative compound R-2 was subjected to four-successive sweeping evaluations of one electron oxidation, and the results indicate that, as shown in FIG. 1B, a reversible oxidation wave was obtained. However, the change of the waveform was large and it is considered that the comparative compound R-2 deteriorated due to the repeated sweeping. In the comparative compound R-2, it is considered that thiophene with the high electron donating property is further directly bonded to the amino group with the high electron donating property, so that the activity of proton at β-position in the thiophene part shown below is high and the electrophilic substitution reaction is activated.

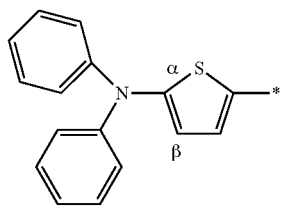 [SMILES: *c1ccc(N(c2ccccc2)c2ccccc2)s1]

The CV measurement was performed in 0.1 M of an ortho-dichlorobenzene solution of tetrabutylammonium perchlorate using Ag/Ag$^+$ as a reference electrode, Pt as an opposite electrode, and glassy carbon as an operation electrode. The sweeping speed was 0.1 V/s. The measurement apparatus is an electrochemical analyzer model 660C manufactured by ALS.

Thus, it is understood that the organic compound according to the present invention has high stability against the oxidation-reduction reaction and is advantageous in durability of the organic photoelectric conversion element against the repeated use.

(3) Evaporation Stability

In the organic photoelectric conversion element according to the present invention, the organic compound layer is preferably manufactured by a vacuum evaporation method. Alternatively, a coating process or the like can be used. Using a vacuum evaporation method enables the formation of the organic compound layer with high purity. In order to form the organic photoelectric conversion element with high performance and high reliability, the organic photoelectric conversion compound preferably has higher purity. In order to increase the purity, a sublimation and purification process is preferably performed. Through the sublimation and purification, not only impurities with different sublimating temperatures but also impurities that do not sublimate, such as inorganic substances, can be removed. The organic compound according to the present invention will not be decomposed in the vacuum evaporation or the sublimation and purification, and is therefore stable.

The example compound A-1 and the comparative compound R-2 were subjected to the sublimation and purification. The example compound A-1 was successfully sublimated and purified at 270° C. The comparative compound R-2, however, was not sublimated and was decomposed at 280° C. This indicates that, in the vacuum evaporation process, the comparative compound R-2 is similarly decomposed in the vacuum evaporation, and therefore is not handled in the vacuum evaporation process. On the other hand, the organic compound according to the present invention is stable thermally, is not decomposed in the vacuum evaporation process, and can manufacture the organic compound layer stably. It is considered that, like the reason why the comparative compound R-2 is less stable against the oxidation-reduction reaction as described in (2) above, the activity of proton at β-position by the high electron donating property is increased and the decomposing reaction becomes more active.

Since the organic compound according to the present invention has the characteristics as described in (1) to (3)

above, the panchromic performance is high, the molar absorption coefficient is high, the stability against the oxidation and reduction is high, and the thermal stability, particularly, the stability in the evaporation is high. Thus, the organic compound according to the present invention exhibits the high evaporation stability when the organic compound is formed into the organic photoelectric conversion film or the organic photoelectric conversion element, and in addition, by using the organic compound as the compound layer of the organic photoelectric conversion film or the organic photoelectric conversion element, the preferable photoelectric conversion characteristic in the entire visible light region can be obtained.

<Organic Photoelectric Conversion Element>

Figure 2:
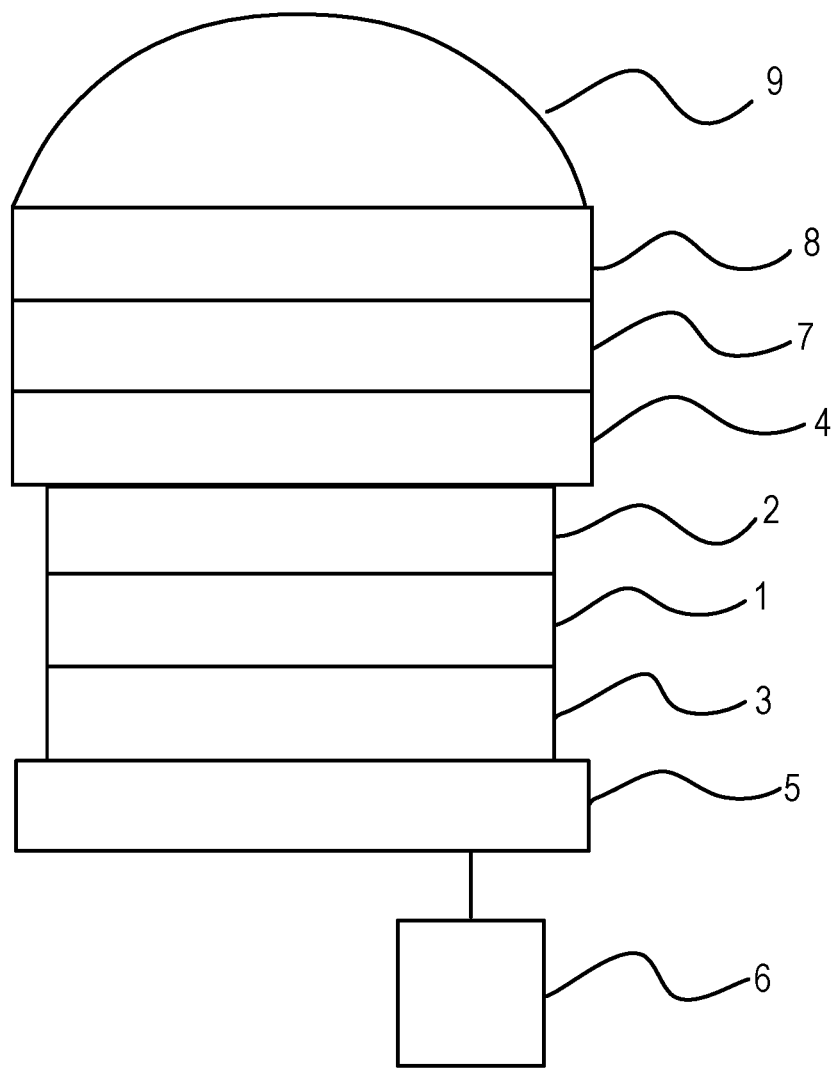
FIG. 2 is a schematic cross-sectional view illustrating one example of an organic photoelectric conversion element.

FIG. 2 is a schematic cross-sectional view illustrating one example of the organic photoelectric conversion element according to the present invention. In the organic photoelectric conversion element in FIG. 2, a first organic compound layer 1 corresponding to a photoelectric conversion unit that converts light into charges is disposed between a hole collecting electrode 4 and an electron collecting electrode 5. The first organic compound layer 1 is a layer that receives light and generates charges in accordance with the amount of received light. From this function, the first organic compound layer 1 is also referred to as a photoelectric conversion layer. The first organic compound layer 1 includes at least the organic compound according to the present invention. The first organic compound layer 1 may include a plurality of kinds of organic compounds. If the first organic compound layer 1 includes a plurality of kinds of organic compounds, the plural kinds of organic compounds may be mixed in one layer or the plural kinds of organic compounds may be included in a plurality of layers. If the plural kinds of organic compounds are included in the plural layers, the layers are preferably stacked in a direction from the electron collecting electrode 5 to the hole collecting electrode 4. The electron collecting electrode 5 is also referred to as an anode, and the hole collecting electrode 4 is also referred to as a cathode.

The first organic compound layer 1 is preferably a layer containing an organic p-type semiconductor or an organic n-type semiconductor, and more preferably containing at least partially a bulk hetero layer (mixed layer) in which an organic p-type semiconductor and an organic n-type semiconductor are mixed. When the first organic compound layer 1 includes the bulk hetero layer, the photoelectric conversion efficiency (sensitivity) can be improved. By including the bulk hetero layer at an optimal mixing ratio, the electron mobility and the hole mobility of the first organic compound layer 1 can be increased and the optical response speed of the organic photoelectric conversion element can be increased.

The first organic compound layer 1 preferably includes fullerene or a fullerene derivative as the organic n-type semiconductor. When the fullerene or the fullerene derivative exists continuously in the first organic compound layer 1, an electron path is formed; thus, the electron transport property is improved and the fast responsiveness of the organic photoelectric conversion element is improved. The fullerene or the fullerene derivative is preferably contained by 40 vol % or more and 85 vol % or less for the volume of the first organic compound layer 1. Examples of the fullerene include fullerene C60, fullerene C70, fullerene C76, fullerene C78, fullerene C80, fullerene C82, fullerene C84, fullerene C90, fullerene C96, fullerene C240, fullerene 540, mixed fullerene, and fullerene nanotube. The fullerene derivative includes a substituent in the fullerene, and examples of this substituent include an alkyl group, an aryl group, and an aromatic heterocyclic group.

The organic p-type semiconductor of the first organic compound layer 1 is a donor type organic semiconductor, and has a property of easily donating electrons, as typified by a hole-transporting organic compound. The organic photoelectric conversion element according to the present invention contains the organic compound according to the present invention as the organic p-type semiconductor (electron donor compound).

The first organic compound layer 1 is preferably a non-light-emitting layer. The non-light-emitting layer refers to a layer whose emission quantum efficiency in a visible light region (wavelength: 400 nm to 730 nm) is 1% or less, preferably 0.5% or less, and more preferably 0.1% or less. It is preferable that the emission quantum efficiency of the first organic compound layer 1 is 1% or less because, in the case of using this first organic compound layer 1 for a sensor or an image pickup element, the sensing performance or the image pickup performance is not affected.

The organic photoelectric conversion element in FIG. 2 may include a second organic compound layer 2 disposed between the first organic compound layer 1 and the hole collecting electrode 4, and a third organic compound layer 3 disposed between the first organic compound layer 1 and the electron collecting electrode 5. The second organic compound layer 2 is a layer that suppresses the entry of electrons from the hole collecting electrode 4 into the first organic compound layer 1, and is also referred to as an electron blocking layer. The electron affinity or lowest unoccupied molecular orbital (LUMO) of the second organic compound layer 2 is preferably small. The organic photoelectric conversion element according to the present invention does not necessarily include the second organic compound layer 2. The third organic compound layer 3 is a layer that suppresses the entry of holes from the electron collecting electrode 5 to the first organic compound layer 1, and is also referred to as a hole blocking layer. The ionizing potential of the hole blocking layer is preferably high. The organic photoelectric conversion element according to the present invention does not necessarily include the third organic compound layer 3.

The hole collecting electrode 4 is an electrode that collects holes among the charges generated in the first organic compound layer 1. The hole collecting electrode 4 is formed of any material as long as the material has high conductivity and transparency. Specifically, metal, metal oxide, metal nitride, metal boride, an organic conductive compound, a mixture thereof, and the like are given. More specifically, conductive metal oxide such as tin oxide doped with antimony or fluorine (ATO or FTO), tin oxide, zinc oxide, indium oxide, indium tin oxide (ITO), or indium zinc oxide (IZO), metal such as gold, silver, chromium, nickel, titanium, molybdenum, tantalum, tungsten, or aluminum, and a conductive compound such as an oxide or a nitride of the above metal (for example, titanium nitride (TiN)) are given). Furthermore, a mixture or a stack of the metal and the conductive metal oxide, an inorganic conductive substance such as copper iodide or copper sulfate, an organic conductive material such as polyaniline, polythiophene, or polypyrrole, and a stack of these materials and ITO or titanium nitride are given. It is particularly preferable that the hole collecting electrode 4 is formed of titanium nitride, molybdenum nitride, tantalum nitride, or tungsten nitride.

The electron collecting electrode 5 is an electrode that collects electrons among the charges generated in the first organic compound layer 1. The electron collecting electrode 5 is disposed closer to a pixel circuit than the hole collecting electrode 4. Specific examples of the material of the electron collecting electrode 5 include ITO, IZO, $SnO_2$, ATO (antimony-doped tin oxide), ZnO, AZO (aluminum-doped zinc oxide), GZO (gallium-doped zinc oxide), $TiO_2$, or FTO (fluorine-doped tin oxide).

A method of forming the electrode can be selected as appropriate in consideration of the compatibility to the electrode material. Specifically, a wet process such as a printing process or a coating process, a physical process such as a vacuum evaporation method, a sputtering method, or an ion plating method, a chemical process such as CVD or a plasma CVD method, or the like may be employed to form the electrode. If the electrode is formed of ITO, the ITO electrode can be formed by, for example, an electron beam method, a sputtering method, a resistive heating evaporation method, a chemical reaction method (sol-gel method and the like), or a method of applying a dispersant of indium tin oxide. Furthermore, the formed ITO electrode can be subjected to a UV-ozone process, a plasma process, or the like. If the electrode is TiN, various methods typified by a reactive sputtering method can be used. The formed TiN electrode can be further subjected to an annealing process, a UV-ozone process, a plasma process, or the like.

In the organic photoelectric conversion element in FIG. 2, the electron collecting electrode 5 is connected to a readout circuit 6. The readout circuit 6 reads out information based on the charges generated in the organic photoelectric conversion unit including the first organic compound layer 1, the second organic compound layer 2, and the third organic compound layer 3, and transmits the information to a signal processing unit (not shown), for example. The readout circuit 6 may be connected to the hole collecting electrode 4.

The organic photoelectric conversion element in FIG. 2 includes an inorganic protective layer 7 on the hole collecting electrode 4. The inorganic protective layer 7 includes, for example, silicon oxide, silicon nitride, aluminum oxide, or the like. The inorganic protective layer 7 can be formed by a vacuum evaporation method, a sputtering method, an atomic layer deposition (ALD) method, or the like.

The organic photoelectric conversion element in FIG. 2 includes a color filter 8 on the inorganic protective layer 7. The color filter 8 may be, for example, a color filter that transmits red light among the visible light. In a case where a plurality of organic photoelectric conversion elements is disposed, one color filter 8 may be disposed on one organic photoelectric conversion element. Alternatively, one color filter 8 may be disposed on a plurality of organic photoelectric conversion elements. The color filter 8 may be disposed in the Bayer array, for example.

The organic photoelectric conversion element in FIG. 2 includes a microlens 9 on the color filter 8. The microlens 9 can condense the incident light into the organic photoelectric conversion element. In the case of using the organic photoelectric conversion elements, one microlens 9 may be disposed on one organic photoelectric conversion element. Alternatively, one microlens 9 may be disposed on a plurality of organic photoelectric conversion elements.

The organic photoelectric conversion element according to the present invention may include a substrate. Examples of the substrate include a silicon substrate, a glass substrate, and a flexible substrate.

In the case where the organic photoelectric conversion element performs the photoelectric conversion, it is preferable to apply voltage between the hole collecting electrode 4 and the electron collecting electrode 5. By reversing the electrode for collecting the holes and the electrode for collecting the electrons, holes may be used as the signal charge in the readout.

<Organic Photoelectric Conversion Apparatus, Optical Area Sensor, Image Pickup Element, and Image Pickup Apparatus>

The organic photoelectric conversion element according to the present invention can receive the light with a different wavelength by setting the constituent material of the first organic compound layer 1 as appropriate. Receiving the light with a different wavelength means that the wavelength region of the light to be converted into electricity by the photoelectric conversion unit is different. In addition, when the plural organic photoelectric conversion elements that receive the light with different wavelengths are stacked, the organic photoelectric conversion apparatus that does not require the color filter 8 can be obtained. Of the plural kinds of organic photoelectric conversion elements in the organic photoelectric conversion apparatus, at least one kind of organic photoelectric conversion element is the organic photoelectric conversion element according to the present invention.

An optical area sensor according to the present invention includes the plural photoelectric conversion elements. The plural photoelectric conversion elements are arranged two-dimensionally in an in-plane direction. In the structure as above, by outputting signals based on the charges generated in the organic photoelectric conversion elements individually, the information expressing the distribution of the light intensity in a predetermined light reception area can be obtained. This optical area sensor may include the organic photoelectric conversion apparatus according to the present invention described above instead of the organic photoelectric conversion element according to the present invention.

The image pickup element according to the present invention includes the organic photoelectric conversion elements each serving as a light receiving pixel, and transistors each connected to the organic photoelectric conversion element. The transistor reads out the charge generated in the organic photoelectric conversion element, and transmits the information based on the readout charge to a sensor unit connected to the image pickup element. The sensor unit is, for example, a CMOS sensor or a CCD sensor. The pieces of information obtained in the light receiving pixels are collected in the sensor unit; thus, an image can be obtained.

Figure 3:
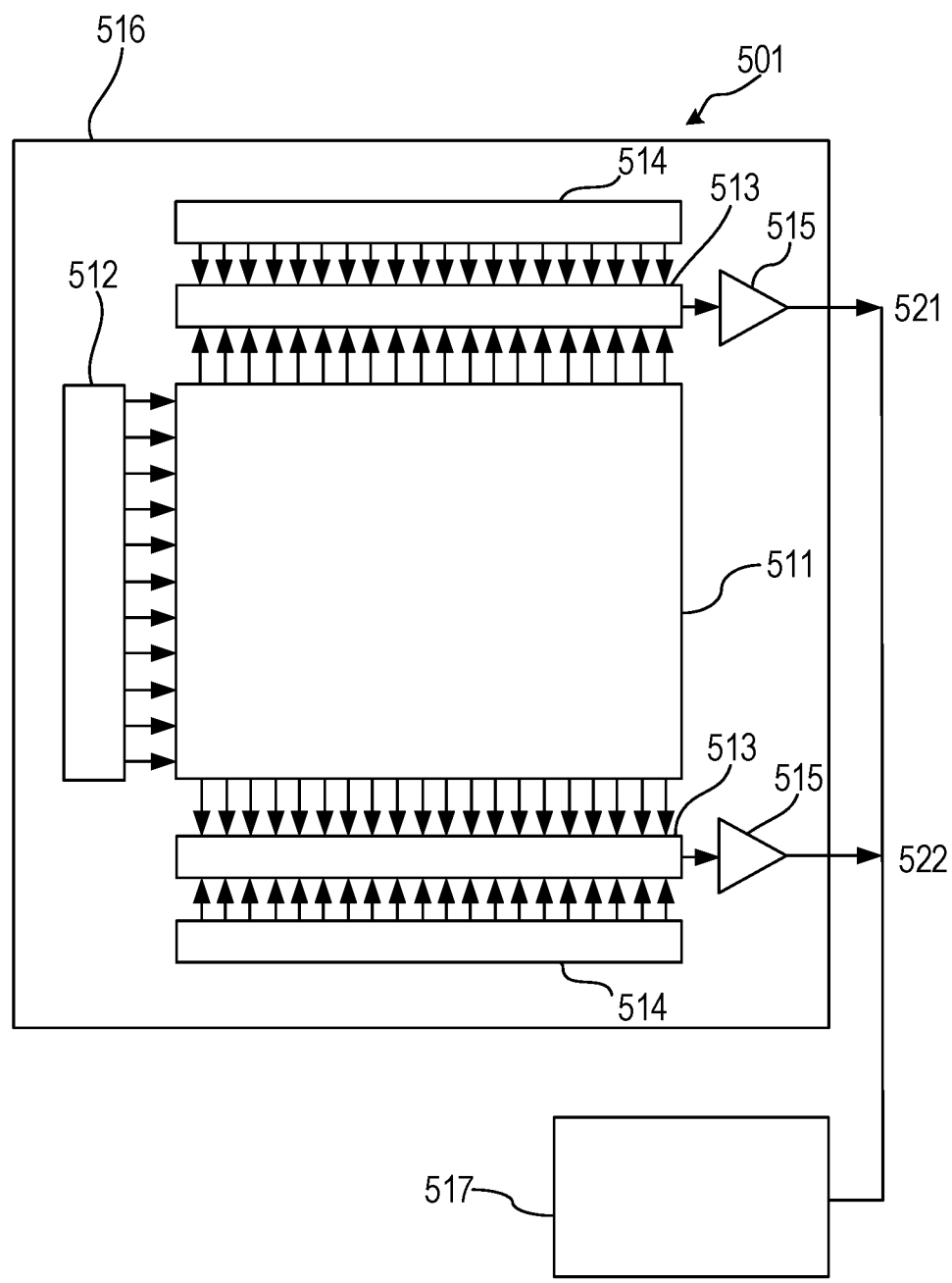
FIG. 3 is a schematic view illustrating one example of an image pickup element.

FIG. 3 is a schematic view illustrating one example of the image pickup element according to the present invention. In FIG. 3, an image pickup element 501 includes an image pickup region 511, a vertical scanning circuit 512, two readout circuits 513, two horizontal scanning circuits 514, and two output amplifiers 515. A region except the image pickup region 511 corresponds to a circuit region 516. In the image pickup region 511, the light receiving pixels are arranged two-dimensionally. The readout circuit 513 includes, for example, a column amplifier, a CDS circuit, an adding circuit, and the like. The signals read out from the pixels in the row selected by the vertical scanning circuit 512 through vertical signal lines are amplified or added, for example. The column amplifier, the CDS circuit, the adding circuit, and the like are arranged for one pixel column or a plurality of pixel columns. The horizontal scanning circuit 514 generates the signals for reading out the signals of the readout circuit 513 in order. The output amplifier 515 amplifies and outputs the signals in the column selected by the horizontal scanning circuit 514. The above structure is merely one structure example of the image pickup element according to the present invention, and the image pickup element according to the present invention is not limited to this example. One set of the readout circuit 513, the horizontal scanning circuit 514, and the output amplifier 515 is formed on an upper side of the image pickup region 511 and another set is formed on a lower side thereof; thus, two output paths can be formed. Alternatively, three or more output paths may be formed. An output signal 521 and an output signal 522 output from the output amplifiers 515 are synthesized as an image signal in a signal processing unit 517.

Figure 4:
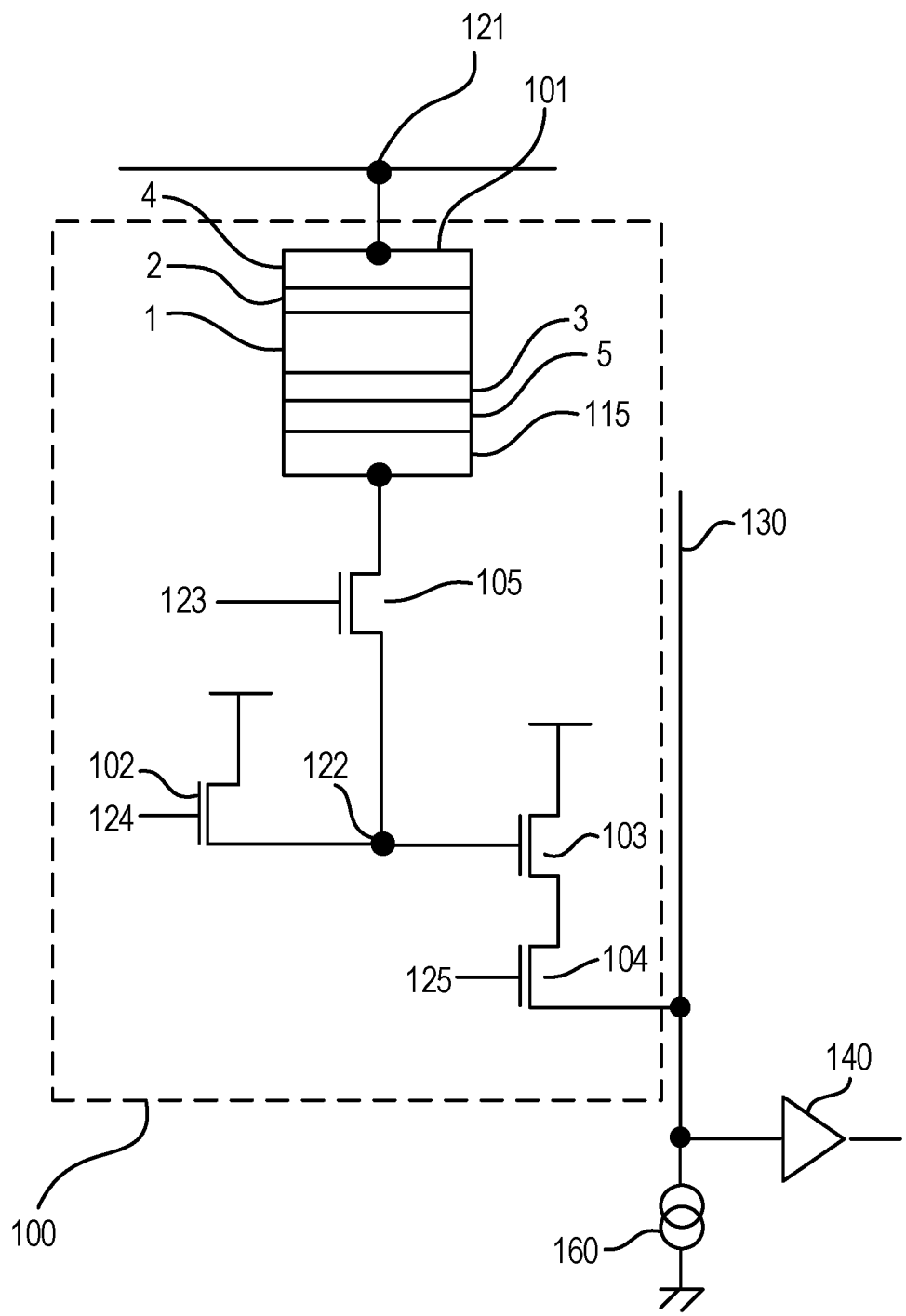
FIG. 4 is an exemplary pixel driving circuit diagram for driving a light receiving pixel of the image pickup element.

FIG. 4 is one example of a pixel driving circuit diagram for driving the light receiving pixel of the image pickup element 501. The light receiving pixel 100 includes an organic photoelectric conversion element 101. A lower surface of a semiconductor layer of the first organic compound layer 1 in the organic photoelectric conversion element 101 is electrically connected to a charge accumulation unit 115 in a semiconductor substrate, and further connected to an amplifier unit 103. The charge accumulation unit 115 in the Si semiconductor substrate is a region where the charges generated in the organic photoelectric conversion element 101 are accumulated, and a P-type region and an N-type region may be formed. With such a structure, the amplifier unit 103 can output the signals generated in the organic photoelectric conversion element 101. The organic photoelectric conversion element 101 and the amplifier unit 103 may be short-circuited. Alternatively, a switch (transfer transistor) 105 may be disposed in an electric path between the organic photoelectric conversion element 101 and the amplifier unit 103 as illustrated in FIG. 4. The switch (transfer transistor) 105 is controlled to be switched on or off by a transfer transistor driving signal (pTX) 123. FIG. 4 illustrates a node 122 expressing an electric connection between the organic photoelectric conversion element 101 and the amplifier unit 103. The node 122 is formed so as to be in an electrically floating state. When the node 122 is in the electrically floating state, the voltage of the node 122 can change depending on the charges generated in the organic photoelectric conversion element 101. Therefore, the signal based on the charges generated in the organic photoelectric conversion element 101 can be input to the amplifier unit 103. The light receiving pixel 100 in FIG. 4 includes a reset unit 102 that resets the voltage in the node 122 in the semiconductor substrate. The reset unit 102 supplies a reset voltage (not shown) to the node 122. The reset unit 102 is, for example, a reset transistor that is electrically connected to the node 122. FIG. 4 illustrates one example of the reset transistor. The reset unit 102 is controlled to be switched on or off by a reset control pulse (pRES) 124. By turning on the reset unit 102, the reset voltage is supplied to the node 122. In FIG. 4, 121 denotes a common wiring connection unit (node A), 130 denotes an output line, 140 denotes a column circuit, 160 denotes a current source, and 104 denotes a selection transistor that transmits a signal selectively to the output line 130. The selection transistor 104 is controlled to be switched on or off by a selection transistor driving signal (pSEL) 125.

The image pickup element may include, for example, an optical filter such as a color filter. In a case where the organic photoelectric conversion element can handle light with a particular wavelength, it is preferable to use an optical filter that can deal with the organic photoelectric conversion element. One optical filter may be provided to one light receiving pixel, or one optical filter may be provided to a plurality of light receiving pixels. The optical filter may be, in addition to a color filter, a long pass filter that transmits wavelengths of more than or equal to an infrared ray, a UV-cut filter, a low pass filter and the like that transmits wavelengths of less than or equal to an ultraviolet ray.

The image pickup element may include an optical member such as a microlens. The microlens is a lens that condenses external light into the photoelectric conversion unit. One optical member may be provided to one light receiving pixel, or one optical member may be provided to a plurality of light receiving pixels. When the plurality of light receiving pixels is provided, it is preferable to provide one optical element for each of the light receiving pixels.

The image pickup apparatus according to the present invention includes an image pickup optical system including a plurality of lenses, and an image pickup element that receives light having passed the image pickup optical system. The image pickup apparatus may include a joint unit that can be jointed to the image pickup optical system, and an image pickup element. More specifically, the image pickup apparatus is a digital camera or a digital still camera. The image pickup apparatus may further include a reception unit that receives external signals. The signals received in the reception unit are signals that control at least any one of the image pickup range of the image pickup apparatus, the start of the image pickup, and the end of the image pickup. The image pickup apparatus may further include a transmission unit that transmits the obtained image to the outside. By including the reception unit and the transmission unit, the image pickup apparatus can be used as a network camera.

EXAMPLES

The present invention will be described in more detail with reference to Examples below; however, the technical range of the present invention is not limited to Examples below.

Example 1

The example compound A-1 was synthesized in accordance with the following scheme.

[Synthesis of Intermediate c-3]

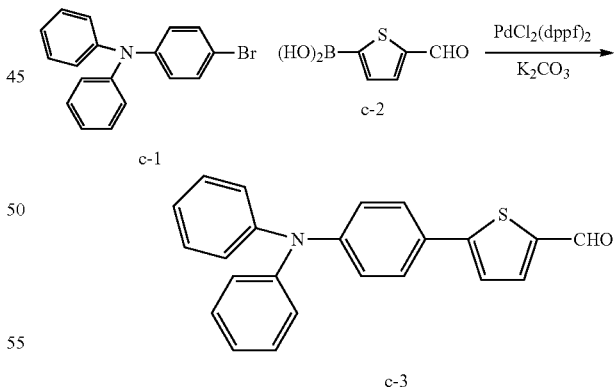

Into a three-neck flask of 100 ml, 1.62 g (5.0 mmol) of the compound c-1, 1.56 g (10.0 mmol) of the compound c-2, 3.45 g of potassium carbonate, 35 ml of toluene, and 35 ml of methanol were added and the mixture was stirred at room temperature in a nitrogen atmosphere. To this mixture, 0.18 g of diphenylphosphinoferrocenepalladiumdichloride was added. Then, the reaction temperature was raised to 90° C., and the mixture was stirred for five hours. After the reaction, the organic layer was extracted with toluene and dried using anhydrous sodium sulfate, and the obtained substance was purified using a silica gel column (developing solvent: mixed solvent of chloroform and heptane), and thus, 1.21 g (yield 68%) of the compound c-3 (yellow solid) was obtained.

[Synthesis of Example Compound A-1]

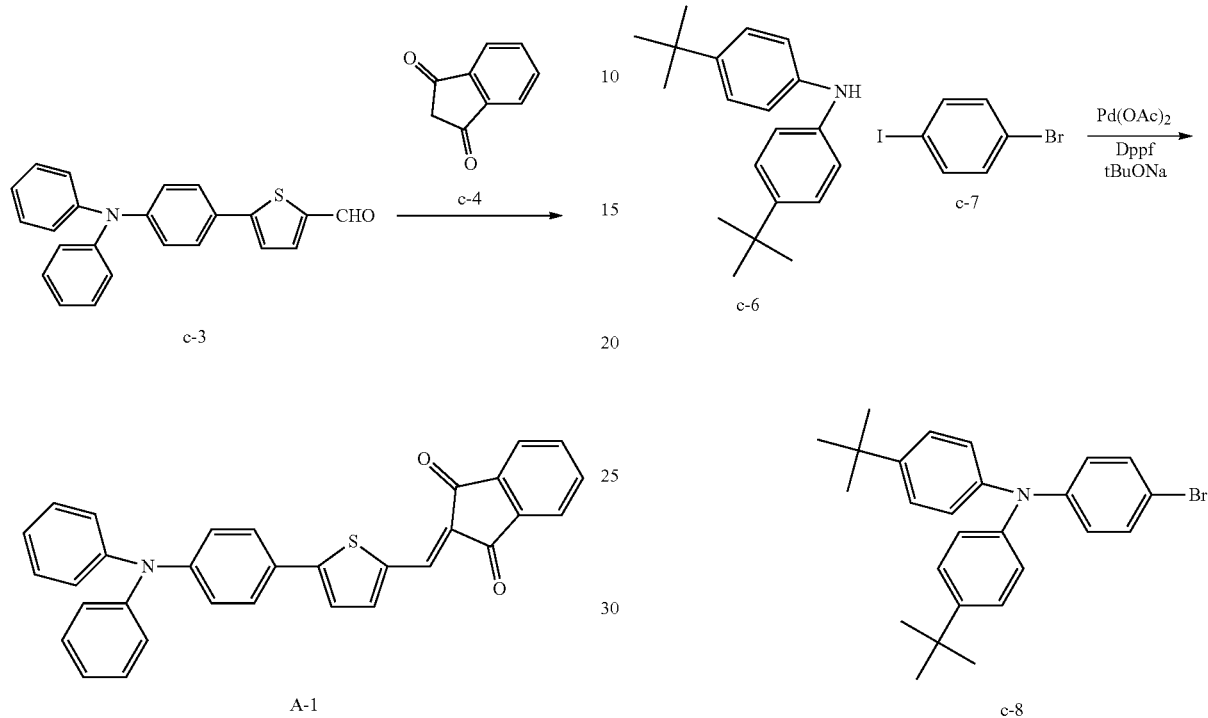

Into a three-neck flask of 100 ml, 1.20 g (3.38 mmol) of the compound c-3, 0.59 g (4.06 mmol) of the compound c-4, and 100 ml of ethanol were added, and the mixture was stirred at room temperature in a nitrogen atmosphere, and to this mixture, 0.05 ml of piperidine was added. Then, the reaction temperature was raised to 90° C., and the mixture was stirred for five hours. After the temperature was reduced to room temperature, the solution was filtered and washed with ethanol. The obtained substance was purified using a silica gel column (developing solvent: mixed solvent of chloroform and heptane), and thus, 1.34 g (yield 82%) of the example compound A-1 (red purple solid) was obtained. In accordance with a mass spectrometry, 483 that is M$^+$ of the example compound A-1 was confirmed.

Example 2

An example compound A-2 was synthesized in accordance with the following scheme.

[Synthesis of Intermediate c-8]

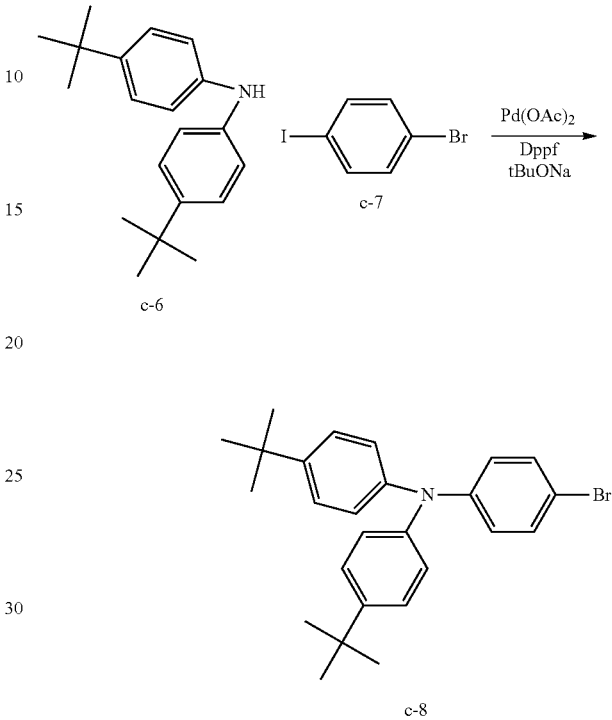

Into a three-neck flask of 100 ml, 5.60 g (20.0 mmol) of the compound c-6, 6.70 g (24.0 mmol) of the compound c-7, 3.84 g (40.0 mmol) of sodium t-butoxy, and 120 ml of toluene were added, and the mixture was stirred at room temperature in a nitrogen atmosphere, and to this mixture, 0.55 g of 1,1'-bis(diphenylphosphino)ferrocene and 0.12 g of palladium acetate were added. Then, the reaction temperature was raised to 85° C., and the mixture was stirred for six hours. After the reaction, the organic layer was extracted with toluene and dried using anhydrous sodium sulfate, and the obtained substance was purified using a silica gel column (developing solvent: mixed solvent of toluene and heptane), and thus, 5.75 g (yield 66%) of the compound c-8 (white solid) was obtained.

[Synthesis of Intermediate c-9]

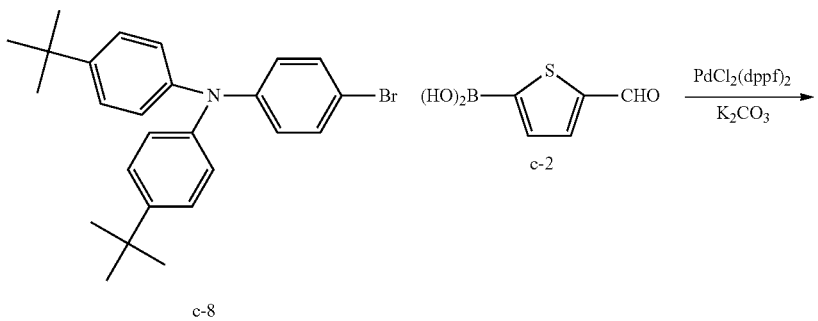

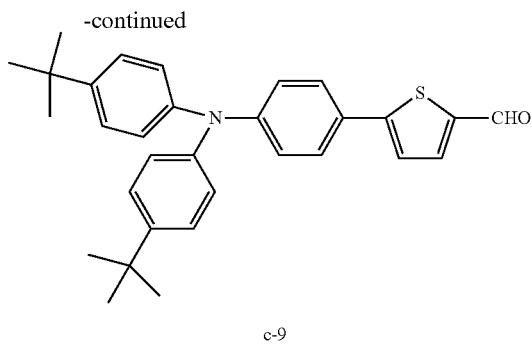

c-9

Into a three-neck flask of 100 ml, 2.18 g (5.0 mmol) of the compound c-8, 1.56 g (10.0 mmol) of the compound c-2, 3.45 g of potassium carbonate, 35 ml of toluene, and 35 ml of methanol were added, and the mixture was stirred at room temperature in a nitrogen atmosphere, and to this mixture, 0.18 g of 1,1'-bis(diphenylphosphino)ferrocenepalladiumdichloride was added. Then, the reaction temperature was raised to 90° C., and the mixture was stirred for six hours. After the reaction, the organic layer was extracted with toluene and dried using anhydrous sodium sulfate, and the obtained substance was purified using a silica gel column (developing solvent: mixed solvent of chloroform and heptane), and thus, 1.47 g (yield 63%) of the compound c-9 (yellow crystal) was obtained.

[Synthesis of Example Compound A-2]

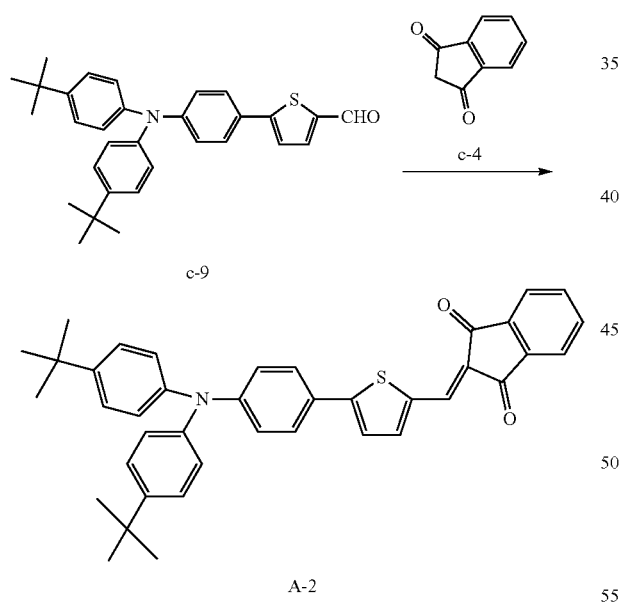

Into a three-neck flask of 100 ml, 0.93 g (2.0 mmol) of the compound c-3, 0.35 g (2.4 mmol) of the compound c-4, and 30 ml of ethanol were added, and the mixture was stirred at room temperature in a nitrogen atmosphere, and to this mixture, 0.05 ml of piperidine was added. Then, the reaction temperature was raised to 90° C., and the mixture was stirred for five hours. After the temperature was reduced to room temperature, the solution was filtered and washed with ethanol. The obtained substance was purified using a silica gel column (developing solvent: mixed solvent of chloroform and heptane), and thus, 0.92 g (yield 77%) of the example compound A-2 (red purple solid) was obtained. In accordance with a mass spectrometry, 595 that is $M^+$ of the example compound A-2 was confirmed.

Example 3

An example compound A-10 was synthesized in accordance with the following scheme.

[Synthesis of Intermediate c-11]

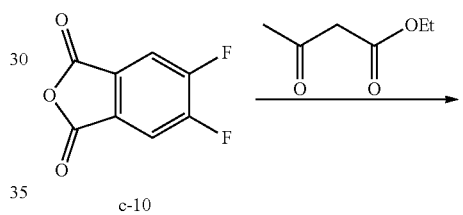

c-10

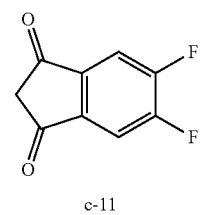

c-11

Into a three-neck flask of 100 ml, 2.50 g (13.6 mmol) of the compound c-10 and 10 ml of acetic anhydride were added, and the mixture was stirred at room temperature in a nitrogen atmosphere. To this mixture, 3.00 g of triethyl amine was dropped and then, 1.90 g (15.0 mmol) of ethyl acetoacetate was dropped slowly. The mixture was stirred at room temperature for five hours. After the mixture was cooled with ice, 7 g of ice was added and 6 ml of concentrated hydrochloric acid was dropped slowly. After the mixture was stirred at room temperature for three hours, the mixture was stirred at 60° C. for one hour. After the mixture was cooled to room temperature, the mixture was filtered and washed with water and acetone in order; thus, 1.77 g (yield 77%) of the compound c-11 (white yellow solid) was obtained.

[Synthesis of Example Compound A-10]

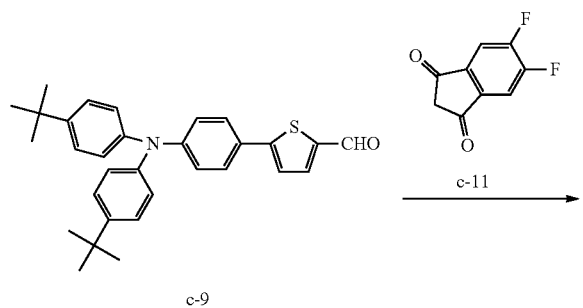

c-9

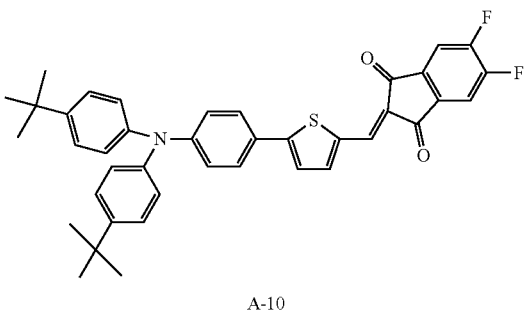

A-10

Into a three-neck flask of 100 ml, 0.47 g (1.0 mmol) of the compound c-9, 0.27 g (1.5 mmol) of the compound c-11, and 20 ml of ethanol were added, and the mixture was stirred at room temperature in a nitrogen atmosphere, and to this mixture, 0.03 ml of piperidine was added. Then, the reaction temperature was raised to 90° C., and the mixture was stirred for five hours. After the temperature was reduced to room temperature, the solution was filtered and washed with ethanol. The obtained substance was purified using a silica gel column (developing solvent: mixed solvent of toluene and heptane), and thus, 0.23 g (yield 36%) of the example compound A-10 (red purple crystal) was obtained. In accordance with a mass spectrometry, 631 that is $M^+$ of the example compound A-10 was confirmed.

Examples 4 to 10

The example compounds shown in Table 2 were synthesized in a manner similar to Example 1 except that a tertiary amine halogen body, thiophene boric acid, and an indane derivative show in Table 2 were used instead of c-1, c-2, and c-4, respectively.

TABLE 2

| Example | Example compound | tertiary amine halogen body | thiophene boric acid | indane derivative |
|---|---|---|---|---|
| 4 | A-3 | | | |
| 5 | A-6 | | | |
| 6 | A-7 | | | |

TABLE 2-continued

| Example | Example compound | tertiary amine halogen body | thiophene boric acid | indane derivative |
|---|---|---|---|---|
| 7 | A-17 | | | |
| 8 | B-2 | | | |
| 9 | D-1 | | | |
| 10 | D-4 | | | |

Examples 11 to 19, and Comparative Examples 1 to 3

Compounds d-1 to d-3 used in the examples and comparative examples are shown below. Note that the compounds R-1 and R-2 used in the comparative examples are the compound R-1 according to Chemical Communications 2012, vol. 48 (71), p. 8907-8909 and the compound R-2 according to Japanese Patent Application Laid-Open No. 2011-77198.

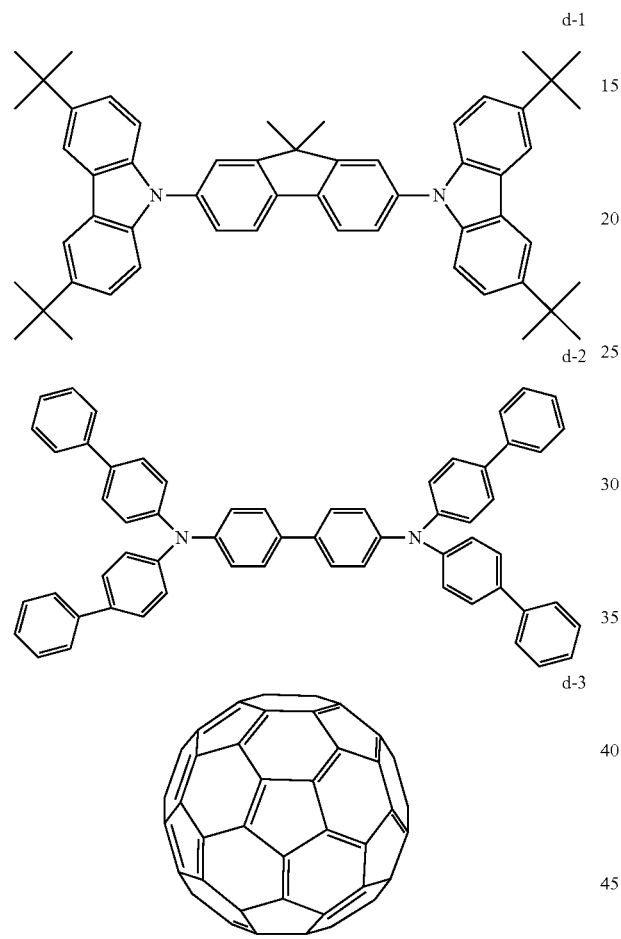

Example 11

The photoelectric conversion element in which the hole collecting electrode 4, the electron blocking layer (second organic compound layer 2), the photoelectric conversion layer (first organic compound layer 1), the hole blocking layer (third organic compound layer 3), and the electron collecting electrode 5 were formed in this order on a substrate was manufactured in accordance with a method described below.

First, a film of indium tin oxide was formed on a Si substrate, and the film was patterned as desired; thus, the hole collecting electrode 4 was formed. The film thickness of the hole collecting electrode 4 was 100 nm. The substrate provided with the hole collecting electrode 4 was used as an electrode-attached substrate in a process below.

On the electrode-attached substrate, the organic compound layers 1 to 3 and the electron collecting electrode 5 shown in Table 3 were formed successively. The organic compound layers 1 to 3 were formed in a vacuum evaporation method. In the first organic compound layer 1, the example compound A-1 as the electron donor material and the compound d-3 as the electron acceptor compound were evaporated with a volume ratio of the example compound A-1: the compound d-3 is 25:75. Note that the electron collecting electrode 5 opposed to the hole collecting electrode 4 had an electrode area of 3 mm$^2$. Thus, the organic photoelectric conversion element was obtained.

TABLE 3

| | Constituting material | Thickness [nm] |
|---|---|---|
| Electron collecting electrode 5 | IZO | 30 nm |
| Third organic compound layer 3 | d-3(C60) | 50 nm |
| First organic compound layer 1 | Example compound A-1:d-3(C60) = 25:75 | 400 nm |
| Second organic compound layer 2 | d-1 | 100 nm |
| Hole collecting electrode 4 | IZO | 100 nm |

Examples 12 to 19, and Comparative Examples 1 to 3

The organic photoelectric conversion element was obtained similarly to Example 11 except that the electron donor material in the first organic compound layer 1 and the material of the second organic compound layer 2 were changed as shown in Table 4.

TABLE 4

| | Electron donor compound | Second organic compound layer 2 | Relative value of external quantum efficiency |
|---|---|---|---|
| Example 12 | A-2 | d-1 | A |
| Example 13 | A-3 | d-1 | A |
| Example 14 | A-7 | d-1 | A |
| Example 15 | D-4 | d-1 | B |
| Example 16 | A-1 | d-2 | A |
| Example 17 | A-2 | d-2 | A |
| Example 18 | A-3 | d-2 | A |
| Example 19 | A-6 | d-2 | B |
| Comparative Example 1 | R-1 | d-1 | C |
| Comparative Example 2 | R-1 | d-2 | C |
| Comparative Example 3 | R-2 | d-1 | Element was not formed because R-2 was decomposed |

[Evaluation on Organic Photoelectric Conversion Element]

To the obtained element, a voltage of 5 V was applied and the external quantum efficiency at this time was measured. The external quantum efficiency was calculated by, in a state where a voltage of 5 V was applied between the hole collecting electrode 4 and the electron collecting electrode 5, delivering single color light with an intensity of 50 μW/cm$^2$ for each wavelength to the element and measuring the photocurrent density at this time. Here, the photocurrent density was obtained by subtracting the dark current density when the light is blocked, from the current density when the light is delivered. The single color light used to measure the photocurrent density is obtained by making the white light emitted from a xenon lamp (apparatus name: XB-50101AA-A, manufactured by USHIO INC.) monochromatic through a monochrometer (apparatus name: MC-10N, manufactured by Ritu Oyo Kougaku Co., Ltd.). The voltage was applied to the element and the current to the element was measured using a source meter (apparatus name: R6243, manufactured by ADVANTEST CORPORATION). In addition, in the measurement of the absorption coefficient in the element and the external quantum efficiency, the light was delivered vertically to the element from the upper electrode (electron collecting electrode 5) side.

The external quantum efficiency of the organic photoelectric conversion elements according to Examples 12 to 19 and Comparative Examples 1 to 3 at a wavelength of 600 nm was evaluated based on the following criteria. Note that a relative value is the value when the external quantum efficiency of the organic photoelectric conversion efficiency according to Example 11 at a wavelength of 600 nm is 1. The results are shown in Table 4.

A: Relative value of the external quantum efficiency is 0.9 or more
B: Relative value of the external quantum efficiency is 0.7 or more and less than 0.9
C: Relative value of the external quantum efficiency is less than 0.7

The results shown in Table 4 indicate that the organic compound according to the present invention can form the element without being decomposed at evaporation and the manufactured organic photoelectric conversion element has the sensitivity in the visible light region on a long wavelength side of 600 nm.

The organic compound according to the present invention has high sensitivity in light absorption, especially the organic compound is highly sensitive to light on a long wavelength side. Therefore, the organic compound according to the present invention can be suitably used for the photoelectric conversion layer of the organic photoelectric conversion element.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An organic photoelectric conversion element comprising:
    an anode;
    a cathode; and
    a photoelectric conversion unit disposed between the anode and the cathode,
    wherein the photoelectric conversion unit includes an organic compound layer including at least an organic compound expressed by general formula 1:

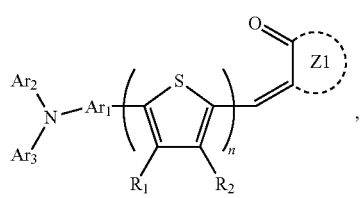

[1]

wherein:
    a partial structure Z1 represents a condensed polycyclic group that may include a nitrogen atom in a skeleton, and that includes at least one of a five-membered ring and a six-membered ring, and the partial structure Z1 may include, as a substituent, a carbonyl group, a dicyanovinylidene group, a halogen atom, a cyano group, an alkyl group, an alkoxy group, an aromatic heterocyclic group, and/or an aryl group;
    $R_1$ and $R_2$ represent a hydrogen atom, an alkyl group, aryl group, an aromatic heterocyclic group, a halogen group, or a cyano group, $Ar_1$ represents a phenylene group, a biphenylene group, or a naphthylene group, and $Ar_2$ and $Ar_3$ independently represent any one of a phenyl group, a biphenyl group, and a naphthyl group, and $Ar_1$ to $Ar_3$ may include, as a substituent, a halogen atom, a cyano group, an alkyl group, an alkoxy group, an aromatic heterocyclic group, and/or an aryl group; and
    n represents an integer of 1 to 4.

2. The organic photoelectric conversion element according to claim 1, wherein the organic compound layer includes an organic n-type semiconductor.

3. The organic photoelectric conversion element according to claim 2, wherein the organic n-type semiconductor is fullerene or a fullerene derivative.

4. An optical area sensor comprising a plurality of organic photoelectric conversion elements, wherein:
    each organic photoelectric conversion element is the organic photoelectric conversion element according to claim 1; and
    the organic photoelectric conversion elements are arranged two-dimensionally in an in-plane direction.

5. An organic photoelectric conversion apparatus comprising a plurality of organic photoelectric conversion elements that have different reception light wavelengths, wherein:
    at least one organic photoelectric conversion element among the plurality of organic photoelectric conversion elements is the organic photoelectric conversion element according to claim 1; and
    the plurality of organic photoelectric conversion elements are stacked.

6. An optical area sensor comprising a plurality of photoelectric conversion apparatuses, wherein:
    each photoelectric conversion apparatus is the photoelectric conversion apparatus according to claim 5; and
    the photoelectric conversion apparatuses are arranged two-dimensionally in an in-plane direction.

7. An image pickup element comprising a plurality of organic photoelectric conversion elements, and transistors each connected to each of the organic photoelectric conversion elements, wherein:
    the organic photoelectric conversion element is the organic photoelectric conversion element according to claim 1; and
    each of the organic photoelectric conversion elements is a light receiving pixel.

8. The image pickup element according to claim 7, comprising an optical filter for the light receiving pixel.

9. The image pickup element according to claim 8, wherein the optical filter is one of a long pass filter that transmits wavelengths more than or equal to an infrared ray, and a low pass filter that transmits wavelengths of less than or equal to an ultraviolet ray.

10. The image pickup element according to claim 7, further comprising an optical member disposed in accordance with each of the light receiving pixels.

11. An image pickup apparatus comprising an image pickup optical system, and an image pickup element that receives light having passed the image pickup optical system, wherein the image pickup element is the image pickup element according to claim 7.

12. The image pickup apparatus according to claim 11, further comprising a joint unit that can be jointed with the image pickup optical system.

13. The image pickup apparatus according to claim 11, wherein the image pickup apparatus is a digital camera or a digital still camera.

14. The image pickup apparatus according to claim 11, further comprising a reception unit that receives a signal from outside, wherein the signal is a signal controlling any of an image pickup range, a start of image pickup, and an end of image pickup.

15. The image pickup apparatus according to claim 11, further comprising a transmission unit that transmits an obtained image to outside.

16. The organic compound according to claim 1, wherein the partial structure Z1 may include, as the substituent, a dicyanovinylidene group, a halogen atom, a cyano group, an alkyl group, an alkoxy group, an aromatic heterocyclic group, and/or an aryl group.

17. The organic compound according to claim 16, wherein, in the general formula 1, the partial structure Z1 is a structure expressed by any one of general formulae 11 to 19:

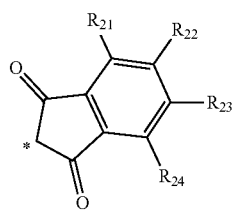

[11]

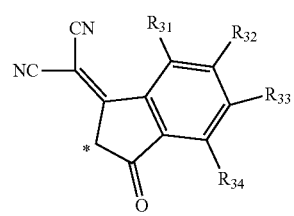

[12]

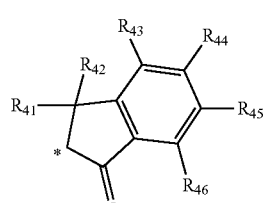

[13]

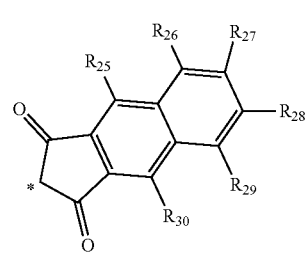

[14]

-continued

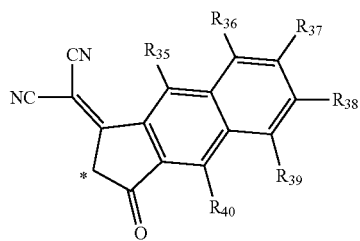

[15]

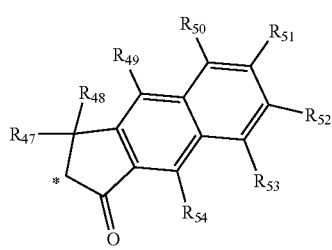

[16]

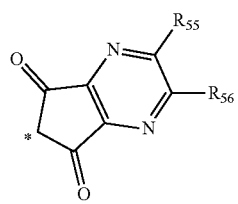

[17]

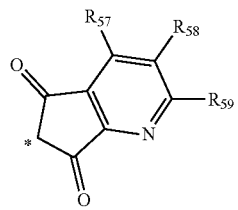

[18]

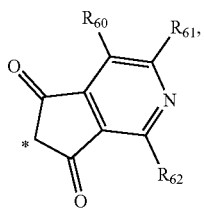

[19]

wherein $R_{21}$ to $R_{62}$ are each independently selected from the group consisting of a hydrogen atom, a halogen atom, a cyano group, an alkyl group.

18. An organic photoelectric conversion element comprising:
   an anode;
   a cathode; and
   a photoelectric conversion unit disposed between the anode and the cathode,
   wherein the photoelectric conversion unit includes an organic compound layer including at least an organic compound expressed by general formula 1:

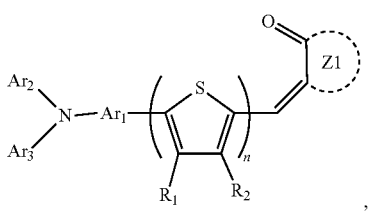

[1]

wherein:

a partial structure Z1 represents a condensed polycyclic group that may include a nitrogen atom in a skeleton, and that includes at least one of a five-membered ring and a six-membered ring, and the partial structure Z1 may include, as a substituent, a carbonyl group, a dicyanovinylidene group, a halogen atom, a cyano group, an alkyl group, an alkoxy group, an aromatic heterocyclic group, and/or an aryl group;

$R_1$ and $R_2$ represent an alkyl group, aryl group, an aromatic heterocyclic group, a halogen group, or a cyano group, $Ar_1$ represents an arylene group or a divalent aromatic heterocyclic group, and $Ar_2$ and $Ar_3$ represent an aryl group or an aromatic heterocyclic group, and $Ar_1$ to $Ar_3$ may include, as a substituent, a halogen atom, a cyano group, an alkyl group, an alkoxy group, an aromatic heterocyclic group, and/or an aryl group;

n represents an integer of 1 to 4; and the partial structure Z1 is a structure expressed by any one of general formulae 11 to 19:

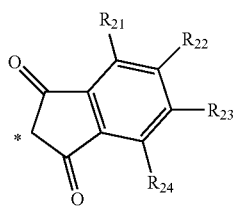

[11]

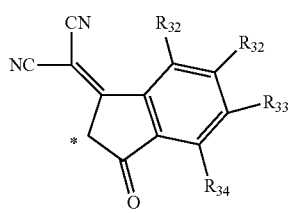

[12]

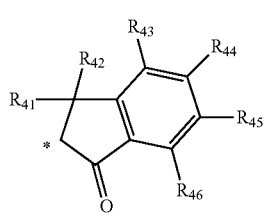

[13]

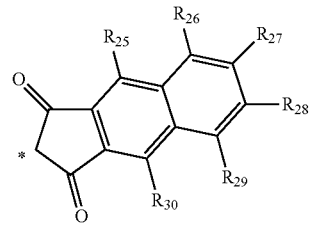

[14]

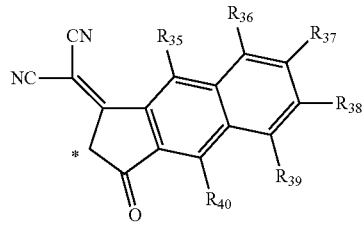

[15]

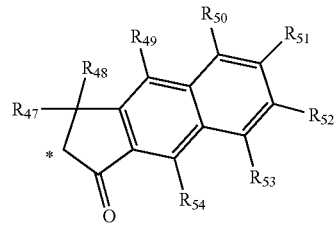

[16]

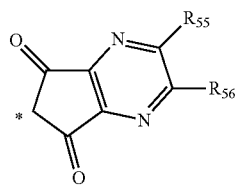

[17]

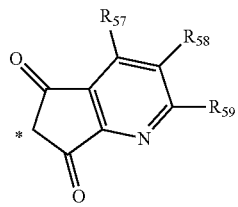

[18]

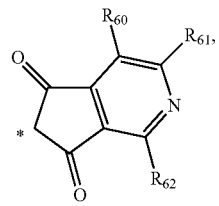

[19]

wherein $R_{21}$ to $R_{62}$ are each independently selected from the group consisting of a hydrogen atom, a halogen atom, a cyano group, an alkyl group, an alkoxy group, an aromatic heterocyclic group, and an aryl group.

19. The organic photoelectric conversion element according to claim 18, wherein in the general formula 1, $Ar_1$ represents a phenylene group, a biphenylene group, or a naphthylene group, and $Ar_2$ and $Ar_3$ independently represent any one of a phenyl group, a biphenyl group, and a naphthyl group.

* * * * *